United States Patent [19]

Peterson et al.

[11] Patent Number: 4,983,189

[45] Date of Patent: * Jan. 8, 1991

[54] METHODS AND APPARATUS FOR MOVING AND SEPARATING MATERIALS EXHIBITING DIFFERENT PHYSICAL PROPERTIES

[75] Inventors: Stephen C. Peterson; Owen D. Brimhall; Thomas J. McLaughlin, al of Salt Lake City; Charles D. Baker, Lehi; Sam L. Sparks, Alpine, all of Utah

[73] Assignee: Technical Research Associates, Inc., Salt Lake City, Utah

[*] Notice: The portion of the term of this patent subsequent to Jul. 26, 2005 has been disclaimed.

[21] Appl. No.: 224,441

[22] Filed: Jul. 25, 1988

Related U.S. Application Data

[63] Continuation of Ser. No. 832,248, Feb. 21, 1986, Pat. No. 4,759,775.

[51] Int. Cl.$^5$ .............................................. B01D 43/00
[52] U.S. Cl. ........................................ 55/15; 55/277; 210/718; 210/738; 210/748; 210/799; 210/188; 366/127; 406/198
[58] Field of Search ...................... 472/20; 55/15, 277; 209/345, 422; 210/702, 718, 738, 748, 799, 188, DIG. 5; 198/630; 406/168, 197, 198; 366/127

[56] References Cited

U.S. PATENT DOCUMENTS

| | | | |
|---|---|---|---|
| 3,625,884 | 12/1971 | Waltrip | 210/19 |
| 3,650,094 | 3/1972 | Goodwin | 55/277 |
| 4,013,552 | 3/1977 | Kreuter | 210/12 |
| 4,055,491 | 10/1977 | Porath-Furedi et al. | 210/19 |
| 4,280,823 | 7/1981 | Szonntagh | 55/15 |
| 4,346,011 | 8/1982 | Brownstein | 210/748 |
| 4,390,976 | 6/1983 | Eynck | 367/153 |
| 4,398,925 | 8/1983 | Trinh et al. | 55/15 |
| 4,523,682 | 6/1985 | Barmatz et al. | 209/638 |

FOREIGN PATENT DOCUMENTS

AU83/00152  10/1983  PCT Int'l Appl. .

OTHER PUBLICATIONS

Apfel, Robert E., "Acoustic Levitation for Studying Liquids and Biological Materials," Naval Research Reviews, pp. 30-40 (1978).
Baker, N. Vashon, "Segregation and Sedimentation of Red Blood Cells in Ultrasonic Standing Waves," Nature, vol. 239, pp. 398–399 (Oct. 13, 1972).
Barmatz, M. B. et al., "Phase Modulation Stops Levitated Sample Rotation," Invention Report prepared by J. T. English for NASA's Jet Propulsion Laboratory, NASA Tech. Brief, vol. 8 No. 2, Item #71 from JPL (List continued on next page.)

Primary Examiner—W. Gary Jones
Attorney, Agent, or Firm—Workman, Nydegger & Jensen

[57] ABSTRACT

Methods and apparatus for controlling the movement of materials having different physical properties when one of the materials is a fluid. The invention does not rely on flocculation, sedimentation, centrifugation, the buoyancy of the materials, or any other gravity dependent characteristic, in order to achieve its desired results. The methods of the present invention provide that a first acoustic wave is propagated through a vessel containing the materials. A second acoustic wave, at a frequency different than the first acoustic wave, is also propagated through the vessel so that the two acoustic waves are superimposed upon each other. The superimposition of the two waves creates a beat frequency wave. The beat frequency wave comprises pressure gradients dividing regions of maximum and minimum pressure. The pressure gradients and the regions of maximum and minimum pressure move through space and time at a group velocity. The moving pressure gradients and regions of maximum and minimum pressure act upon the materials so as to move one of the materials towards a predetermined location in the vessel. The present invention provides that the materials may be controllably moved toward a location, aggregated at a particular location, or physically separated from each other.

43 Claims, 6 Drawing Sheets

OTHER PUBLICATIONS

Invention Report, NPO-16002/5412, pp. 1 to 3 (prepared Winter 1983).

Barmatz, Martin B. and Allen, James L., "Acoustic Translation of an Acoustically Levitated Sample," NASA Tech Briefs, May/Jun. 1986, p. 144.

Barmatz, Martin B. and Gaspar, Mark S., "Acoustic Levitator Maintains Resonance," NASA Tech Briefs, May/Jun. 1986, p. 145.

Crum, Lawrence A. et al., "Motion of Bubbles in a Stationary Sound Field," The Journal of the Acoustical Society of America, vol. 48, No. 1(2), pp. 181-189 (1970).

Dyson, Mary, "Flow of Red Blood Cells Stopped by Ultrasound," Nature, vol. 232, pp. 572-573 (Aug. 20, 1971).

Eller, Anthony, "Force on a Bubble in a Standing Acoustic Wave," The Journal of the Acoustical Society of America, vol. 43, No. 1, pp. 170-171 (1968).

Fairbank, Jr., William M., "A New Noninvasive Technique for Cardiac Pressure Measurement: Resonant Scattering of Ultrasound from Bubbles," IEEE Transactions of Biomedical Engineering, vol. BME-24, No. 2, pp. 107-110 (1977).

Howkins, S. D. et al., "The Effect of Focused Ultrasound on Human Blood," Ultrasonics, pp. 174-176 (Jul. 1970).

Jacobi, N. et al., "Free Oscillations of a Large Drop in Space," Paper Provided by American Institute of Aeronautics and Astronautics, Inc., pp. 1-10 (1979).

Lewin, Peter A., "Acoustically Induced Shear Stresses in the Vicinity of Microbubbles in Tissue," J. Acoust. Soc. Am. 71(3), pp. 729-734 (Mar. 1982).

King, Louis V., F.R.S., "On the Acoustic Radiation Pressure on Spheres," paper presented to McGill University, Montreal (received Jun. 14, 1934), pp. 212-240.

Maidanik, G. et al., "Acoustical Radiation Pressure Due to Incident Plane Progessive Waves on Spherical Objects," The Journal of the Acoustical Society of America, vol. 29, No. 6 (Jun. 1957).

Maidanik, G., "Acoustical Radiation Pressure Due to Incident Plane Progressive Waves on Spherical Objects," The Journal of the Acoustical Society of America, vol. 29, No. 8 (Aug., 1957).

Pinamonti, S. et al., "Further Experiments in Pulse-Echo Sonication of Erythrocytes in Vitro," p. 2101 (no date).

Sykes, Stephen M. et al., "Blood Clotting as an Endpoint in Ultrasound Research," (no date), Division of Biological Effects Bureau of Radiological Health, Food and Drug Administration, pp. III-6 to III-13.

Varanasi, Usha et al., "A Novel Microtechnique for the Measurement of Acoustic Properties of Lipids," Chemistry and Physics of Lipids 19, pp. 179-184 (1977).

Wang. C. Y., "Acoustic Streaming of a Sphere Near an Unsteady Source," J. Acoust. Soc. Am. 71(3), pp. 580-584 (Mar. 1982).

Westervelt, P. J., "The Theory of Steady Forces Caused by Sound Waves," Journal of the Acoustical Society of America, vol. 23, No. 4, pp. 312-315 (1951).

Whymark, R. R., "Acoustic Field Positioning for Containerless Processing," Ultrasonics, pp. 251-262 (Nov. 1975).

METHODS AND APPARATUS FOR MOVING AND SEPARATING MATERIALS EXHIBITING DIFFERENT PHYSICAL PROPERTIES

Government Rights

The present invention was developed at least in part pursuant to support received from the United States Department of Energy and the National Heart, Lung, and Blood Institute through cooperative agreements, and the Government of the United States of America has certain nonexclusive rights under those cooperative agreements.

This is a continuation of U.S. patent application Ser. No. 832,248, filed Feb. 21, 1986, now U.S. Pat. No. 4,759,775.

BACKGROUND

1. The Field of the Invention

The present invention is related to methods and apparatus for controlling the movement of materials exhibiting different physical properties by the application of acoustical energy to the materials. More particularly, the present invention is directed to methods and apparatus capable of continuously separating various materials from a fluid flow system when the materials exhibit physical properties, such as acoustical properties, different than the fluid medium.

2. The Prior Art

Numerous fields of modern technology require that materials which are being carried by a fluid system be separated from the liquid. For example, many industrial processes generate waste water which is contaminated by particulate matter. Separation of the particulate matter from the fluid allows the water to be easily disposed of and the particulate matter, if valuable, put to a good use. Furthermore, it is often desirable to separate an immiscible liquid or undissolved gas from a liquid.

The number of occasions in which it is necessary to separate particulates from a fluid medium is so pervasive that an extraordinary amount of attention has been devoted to the development of methods and apparatus to effect such separations.

One of the most rudimentary, yet pervasive, of separation techniques involves simple sedimentation. Sedimentation is the natural settling process wherein the particulates, gas bubbles, or immiscible liquids are separated due to gravitational force. The medium may then be removed by decanting or suction, while taking care not to disturb the particulates which have settled out of the medium.

Sedimentation techniques have the advantage of being simple and inexpensive. Unfortunately, the characteristics of the medium and the particles to be separated are often such that the time required for separation by sedimentation can be so long as to make this technique entirely impractical. Furthermore, if the particles are of a very small size, the particles will never "settle out" due to the Brownian motion of the molecules. Still further, if the carrying liquid is not kept free of any turbulence until sedimentation is complete, the particles will become resuspended. As a result, simple sedimentation techniques are practical only in certain limited situations.

In recognition of the fact that gravitational forces are too weak to effect rapid sedimentation in many instances, a frequent approach utilized in the prior art in order to increase the sedimentation rate of the material is to increase the gravitational force. This may be accomplished by subjecting the particle and medium mixture to centrifugation.

Centrifugation is a technique in which a container holding the particle and medium mixture is spun about a central axis in order to create centrifugal forces extending radially from the central axis. Increasing the speed of rotation will increase the centrifugal force applied to suspended particles, thereby increasing the rate of sedimentation. Modern centrifuges are capable of generating forces many thousands of times greater than gravity.

Yet another general technique used to separate some types of particles from a medium is filtration. Filtration involves the use of a porous filter that allows passage of the medium, while forming a barrier to the particles to be separated out. The speed of filtration can be enhanced by the application of pressure. However, the speed of filtration markedly decreases as a layer of filtered material builds up against the filter. For optimum performance, the filter must be replaced or cleaned frequently.

Each of the foregoing techniques is widely practiced and is extremely useful in many applications. Yet, each technique suffers significant drawbacks which limits its application to many situations.

For example, as mentioned above, gravitational sedimentation is not effective in many instances when the particles or the medium exhibit particular characteristics, such as when the medium is extremely viscous. Although centrifugation often speeds up the process of separation in such cases, centrifugation is often not completely effective; moreover, centrifugation is ill suited either for processing large quantities of a medium and particle mixture or for processing in continuous flow systems.

Filter techniques also suffer ineffectiveness when the particles to be separated from the medium begin to significantly build up on the filter. This build-up, or "caking", reduces the efficiency of the filter; at some point in the filtration process, this caking may completely stop the flow of the medium through the filter. If additional pressure is applied to the medium in order to improve the flow through the filter, damage to some types of separated material, e.g., blood cells, may occur.

Furthermore, filtration is generally ineffective when separating two immiscible liquids or when separating undissolved gases from a liquid. Some additional shortcomings of these traditional approaches may be better appreciated by reference to certain specific applications.

One area in which it is important to separate particles from a medium is in the medical arts. Numerous medical treatments and diagnostic tests, for example, require that blood (or other body fluids) be separated into their particulate and liquid components. Centrifugation has long been used for processing small amounts of blood in test tube sized containers. Such containers are typically filled with blood and placed in a small centrifuge, and then spun so that the blood cells accumulate in one portion of the container, leaving plasma in the upper portion of the container. The plasma is then decanted or suctioned off.

It will be readily appreciated that the use of test tube-sized containers is not very practical when a large amount of blood is to be separated into its plasma and cellular components. Yet, several medical procedures require separation of substantial volumes of blood into the cellular and plasma components.

One such procedure, generally known as "plasma phoresis", involves replacement of most of a patient's plasma with donor plasma or other suitable plasma substitute. This procedure involves removing whole blood from a patient, separating the cellular components from the plasma, discarding the plasma, and resuspending the cellular components in donor plasma. The reconstituted blood is then returned to the patient. Plasma exchange therapy has been successfully used to treat a variety of clinical conditions such as toxemias, drug overdoses, certain types of cancer, rheumatoid arthritis, and disseminated intravascular coagulation.

One attempt to improve the usefulness of centrifugation for use in plasma phoresis has lead to the development of continuous flow centrifuges. Unfortunately, continuous flow centrifuge processes also have serious drawbacks.

For example, the equipment necessary to perform continuous centrifugation is large, bulky, and also relatively expensive. Further, continuous centrifuges require relatively large volumes of blood to operate properly, and blood passing therethrough has a substantial residence time. This characteristic, in turn, mean that the patient must either do without a substantial volume of blood for an extended period of time, or must be provided with a whole blood substitute. Use of a whole blood substitute dilutes the patient's blood, and thus partially negates the aim of plasma phoresis to replace plasma, but not to replace the cellular components of the patient's blood.

Yet another disadvantage when using centrifugation to separate plasma from cellular blood components is that centrifugation causes the cellular components to become very tightly packed which may in itself cause damage to the blood cells. Subsequent reconstitution to whole blood by the addition of donor plasma is difficult to accomplish without causing hemolysis (i.e., damage) of the relatively delicate red blood cells. In any procedure in which biological materials are to be separated for reuse, extreme care must be taken so that the biological materials to be separated are not damaged by the process.

Another example of an area in which it is commonly important to separate another material from a medium involves petroleum-based materials. Oftentimes, a petroleum based product, hereinafter generally referred to as "oil," will be introduced into water during a processing step.

For example, in order to retrieve the maximum amount of oil possible from a particular amount of oil shale (rock having a high oil content), high temperature steam will be applied to the shale so as to extract the oil out from the nonpetroleum substances.

After the process is completed, the condensed steam contains a significant percentage of the oil that has been extracted from the oil shale. Since oil and water are immiscible, these liquids might be separated by the use of sedimentation or centrifugation. However, the same difficulties that were mentioned above are compounded when sedimentation or centrifugation are used to separate two immiscible liquids.

Another example of an area in which there is a need to separate material from the medium is liquid purification. Many times a liquid must be "purified" before it is used. While many applications do not require a degree of purification that is available when distillation purification procedures are used, many applications require that a significant amount of particulate matter be removed from the liquid.

In many applications, this particulate matter will be microscopic-sized particles of dirt. Removal of these dirt particles by sedimentation is impractical for the reasons mentioned earlier.

Filtration techniques are often used to remove such microscopic sized particles of dirt. However, the use of conventional filters to remove particles requires that, as mentioned above, the filter be replaced or cleaned as the particles build up on the filter media. Removal or cleaning of filters is often a time-consuming procedure requiring that the processing of the fluid be discontinued.

Because of the limitations of conventional techniques for separating particles from a medium, a great deal of effort has been directed to developing new techniques as well as improving the conventional techniques. One technique of relatively recent origin is shown in U.S. Pat. No. 4,055,491 issued to Porath-Furedi.

According to the Porath-Furedi patent, ultrasonic standing waves are used to cause flocculation of small particles, such as blood or algae, so that they will settle out of the carrying liquid. The Porath-Furedi patent describes a separation process which submerges an ultrasonic wave generator within a liquid having particles suspended therein and energizing it so that standing wave is established.

The establishment of a standing wave in the medium results in formation of pressure nodes to which the particles tend to migrate; these nodes and antinodes are at right angles to the direction of propagation of the ultrasonic waves, and the nodes are spaced from adjacent nodes by a distance equal to one-half of the wavelength of the ultrasonic wave.

The Porath-Furedi patent utilizes the accumulation of solid particles at the nodes or antinodes to cause flocculation, thereby assisting in simple gravitational sedimentation of the suspended particles when the ultrasonic standing wave is discontinued.

While the use of ultrasonic waves to flocculate particles as disclosed by the Porath-Furedi patent does substantially increase the sedimentation rate of those particles, the process is still quite slow. It also appears that the Porath-Furedi process is limited to intermittent flow "batch" operations. In particular, this process would not be practical in a high volume, or relatively rapid flow, process because of the extended residence time in the device that would be required to remove all of the particulate matter.

A variation of the Porath-Furedi process appears in U.S. Pat. No. 4,398,925 to Trinh et al. relating to the removal of air bubbles from a liquid, such as molten glass. The Trinh et al. process involves application of a particular ultrasonic frequency capable of establishing a standing wave having a single pressure well at a location half way between the bottom and the top of the container of liquid. Bubbles suspended in the liquid are pushed toward the pressure well, where they coalesce to form larger bubbles.

The ultrasonic wave is then interrupted so that the bubbles begin to float upward due to their buoyancy. After the coalesced bubbles have risen above the level of the pressure well, a second ultrasonic frequency is applied so that a second standing wave pattern is established—the second standing wave pattern having two pressure wells. The bubbles are then urged upwardly to the closest of the two pressure wells.

The foregoing process is then repeated. After the bubbles reach the upper pressure well, the ultrasonic generator is switched off so that bubbles continue to rise above the level of that well, and then yet a third ultrasonic frequency is applied, this one having three pressure wells. Again, the bubbles will be urged toward the highest pressure well, at which point the process can be repeated with progressively higher ultrasonic frequencies.

It will be readily appreciated that the Trinh et al. process relies on the buoyancy of the suspended bubbles to move the bubbles between wells during periods when the ultrasonic generator is switched off. Failure of the particles to move beyond the well will result in splitting of the particles and formation of multiple bands. Additionally, as with the Porath-Furedi process, it appears that the Trinh et al. process is primarily a batch process and is not well suited for use in situations such as plasma phoresis where a continuous supply of a medium must be subjected to the process.

Ultrasonic processes also have application in other fluid processing situations. For example, U.S. Pat. No. 4,013,552, issued to Creuter, shows the use of ultrasonic energy transmitted through sewage in order to reduce the size of the particles in the liquid by cavitation. Such cavitation enhances the ability of the particles to be exposed to oxygen and thus accelerate the action of aerobic bacteria. (The term "cavitation" refers to the creation of disturbances in a fluid caused by formation of gas bubbles by the application of acoustic energy.)

U.S. Pat. No. 4,346,011, issued to Brownstein, discloses a process which utilizes ultrasonic waves to flocculate particulate matter so as to prevent the particles from fouling a filter screen. The Brownstein patent, similar to the Creuter patent, appears to use cavitation to achieve its desired result.

In view of the foregoing, it will be appreciated that it would be a significant advancement in the art if methods and apparatus could be provided which are capable of effecting movement and separation of particles from liquids, immiscible liquids from each other, and undissolved gases from a liquid, that avoided the disadvantages of the techniques found in the prior art. It would also be of particular significance if methods and apparatus could be provided which have a high volume throughput, a relatively short residence time, and the ability to effect movement and rapid separation of the particles from the medium.

It would also be a significant improvement in the art to provide methods and apparatus for separating two materials without requiring physical contact with the materials and without causing significant damage to the materials, for example, blood. Furthermore, providing methods and apparatus for controllably moving, agitating, or separating materials of different physical properties, such as size or density, as well as methods which are adaptable to either batch mode or continuous flow systems, would be an important advancement in the art.

BRIEF SUMMARY AND OBJECTS OF THE INVENTION

The present invention is directed to methods and apparatus for moving and separating materials of different physical properties. Examples of such properties include the velocity of acoustic pressure waves through the materials, the size of the particles when one of the materials is particulate matter, and the density of the materials. The methods of the present invention use acoustic pressure waves in the ultrasonic region to aggregate materials having similar physical properties in a location where they may be separated from the remaining material using techniques known in the art.

According to the preferred embodiments of the present invention, two acoustic waves having different frequencies are propagated in opposite directions such that the two waves are superimposed upon one another to form a beat frequency wave. This beat frequency wave exhibits pressure gradients which separate regions of pressure maxima and pressure minima. The materials are segregated since they tend to migrate to the regions of either pressure maxima or pressure minima.

Furthermore, the pressure gradients are capable of moving materials suspended within a fluid medium in a predetermined direction. The movement of the pressure gradients is controlled such that the materials are moved toward a predetermined location. After materials of similar properties have been aggregated at the predetermined location, they may be physically separated from the remaining materials.

It is, therefore, an object of the present invention to provide methods and apparatus capable of separating materials possessing different physical properties from one another.

Another important object of the present invention is to provide methods and apparatus to separate materials having different physical properties from one another without causing damage to the materials, such as the separation of blood cells from plasma.

Still another object of the present invention is to provide methods and apparatus which allows materials having different physical properties to be separated without requiring physical contact within an isolated system containing the materials.

A further object of the present invention is to provide methods and apparatus for separating particulate matter from a fluid medium in either a batch mode or a continuous flow fluid system.

A still further object of the present invention is to provide methods and apparatus for separating immiscible liquids from one another.

Another object of the present invention is to provide methods and apparatus for moving or agitating materials of different physical properties.

Still another object of the present invention is to provide methods and apparatus for separating particles of different sizes, which are contained within a fluid, from each other.

These and other objects of the present invention will become apparent throughout the following description, taken in connection with the accompanying drawings.

DETAILED DESCRIPTION OF THE EMBODIMENTS

A. Introduction

Figure 1:
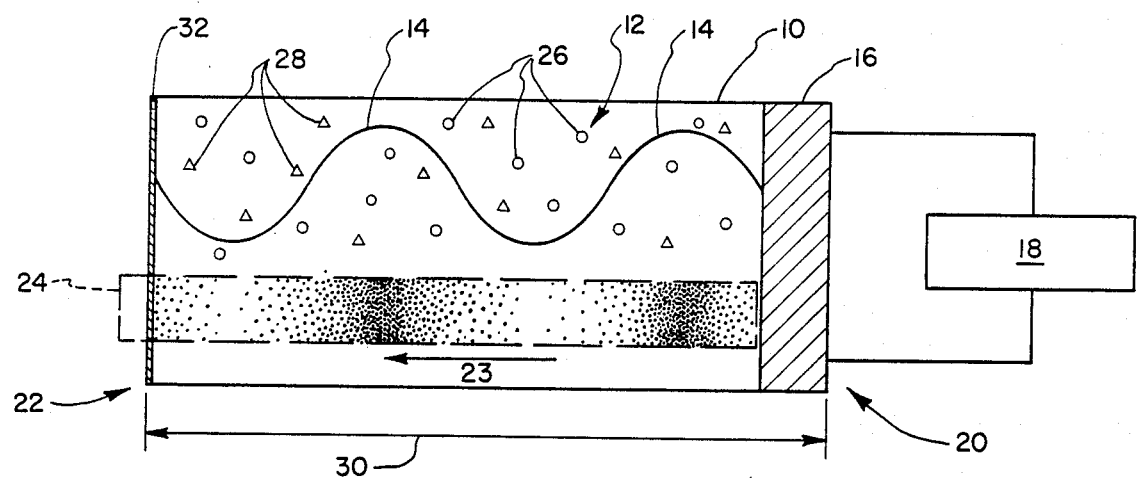
FIG. 1 is a cross-sectional representation of a system through which an acoustic pressure wave is propagated.

In order to achieve the above-mentioned objectives, the present invention utilizes the propagation of acoustic pressure waves propagated through a medium at frequencies in the ultrasonic region. The ultrasonic region is generally considered to be those frequencies which are greater than 20 kilohertz (kHz). However, the portion of the ultrasonic region that will be discussed herein will principally be concerned with those frequencies in the range from about 500 kHz to as high as about 20 megahertz (mHz). However, frequencies higher or lower than this range may be used according to the present invention with the realization that the introduction of cavitation, as will be explained later, is detrimental to the present invention.

In the following general discussion, some of the principles of acoustics are presented as background for gaining an understanding of the present invention. Following the general discussion section, an explanation of the structure and operation of the various embodiments of the present invention is presented. Included with the explanation of the structure and operation of the embodiments are specific examples showing results obtainable when using the embodiments. When reference is made to the drawings, like structures in the drawings will be designated with like reference numerals throughout.

As will be appreciated from the foregoing discussion, the present invention has application in the movement and separation of particles, immiscible liquids, and undissolved gases within a liquid. However, for purposes of clarity, the following description generally refers only to particles; however, it should be understood that an immiscible liquid or gas bubble could also be involved. Thus, when the term "particle" or "particulate" is used, it is not intended to be limiting, but merely representative.

Furthermore, whenever the term "medium", or "media" is used hereinafter, it shall be understood to mean the fluid which is carrying the particles which are desired to be separated from the medium. The embodiments of the present invention which are disclosed herein generally use a liquid as the medium. Further, since the present invention includes the capability of separating materials of different physical properties, such as having different densities or sizes, from a single medium, the following description may refer to a denser and a lighter particle being carried in a particular medium.

B. General Discussion

As will be appreciated by those familiar with the fundamental principles of sound and acoustics, the most basic principles can be readily understood by reference to diagrams schematically showing the propagation and interaction of the acoustic pressure waves within a system. FIGS. 1-5 will now be referred to in order to explain these fundamental principles of sound and acoustics.

FIGS. 1-4 show the response of acoustic pressure waves in a closed system, in this case a closed rectangularly shaped system, represented by 10 in FIGS. 1-4. Within system 10 is contained a propagation material, generally designated 12, through which the acoustic pressure 21 waves are propagated. In FIGS. 1-4, the selected propagation material 12 is water; however, the principles discussed hereinafter apply to whatever material is used as the propagation material.

In FIG. 1, an acoustic pressure wave 14 has been introduced into system 10 by transducer 16 located at a first end of system 10. Transducer 16, converts electrical energy, generated by frequency generator 18, into acoustical energy. Acoustic pressure wave 14 created by transducer 16 travels in a direction, shown by arrow 23, from the first end of the system, generally designated 20, to a second end of the system, generally designated 22.

It will be appreciated that the sine wave representation of the acoustic pressure wave follows from the conventional method of showing an acoustic pressure wave propagating through a medium. However, it should be understood that the acoustic pressure wave is propagating, (i.e., traveling) through the system and that all of the figures schematically represent the acoustic pressure wave at a particular moment in time. In FIG. 1, the particular moment in time shown is when the leading pressure gradient reaches second end 22 of system 10.

It should also be understood that the sine wave representation is meant to indicate areas of increased and decreased pressure within the medium. Also, acoustic pressure waves in a fluid such as water, are actually longitudinal waves, not transverse waves as are generally indicated by the sine waves used in the figures. This principle is best illustrated in the lower portion of system 10 which is separated by the dashed box marked 24.

In dashed box 24, areas of increased pressure are represented by denser stipling, while areas of decreased pressure are represented by lighter stipling. The dots of the stipling are generally representative of the molecules of the medium and their spacing relative one to another.

Within the medium, various particles, gas bubbles, or droplets of an immiscible liquid, are represented by circles and triangles. Particles possessing a density greater than that of the medium are represented by circles, a few of which are designated 26, and particles possessing a density less than that of the medium are represented by triangles, a few of which are designated 28.

FIG. 1 shows the acoustic pressure wave 14 having propagated across the length of system 10. The length of system 10, as shown in FIGS. 1-4 by line 30, is two wavelengths long. The wavelength of a particular frequency is related to the speed at which the acoustic pressure wave 14 propagates through the medium. In the present example, the medium is water which exhibits a longitudinal wave velocity of about 1480 meters per second. The wavelength is related to the frequency and the wave velocity through the medium by Equation A, as set forth below:

$$\lambda = \frac{c}{f} \quad \text{(A)}$$

Where:
$\lambda$ = Wavelength
$c$ = Velocity of the wave in the medium
$f$ = Frequency of the wave Thus, if the frequency of the wave propagated through the medium of FIG. 1 is 3 mHz, then the wavelength is about 493 microns and the length of the system, designated by line 30, is about 986 microns.

Figure 2:
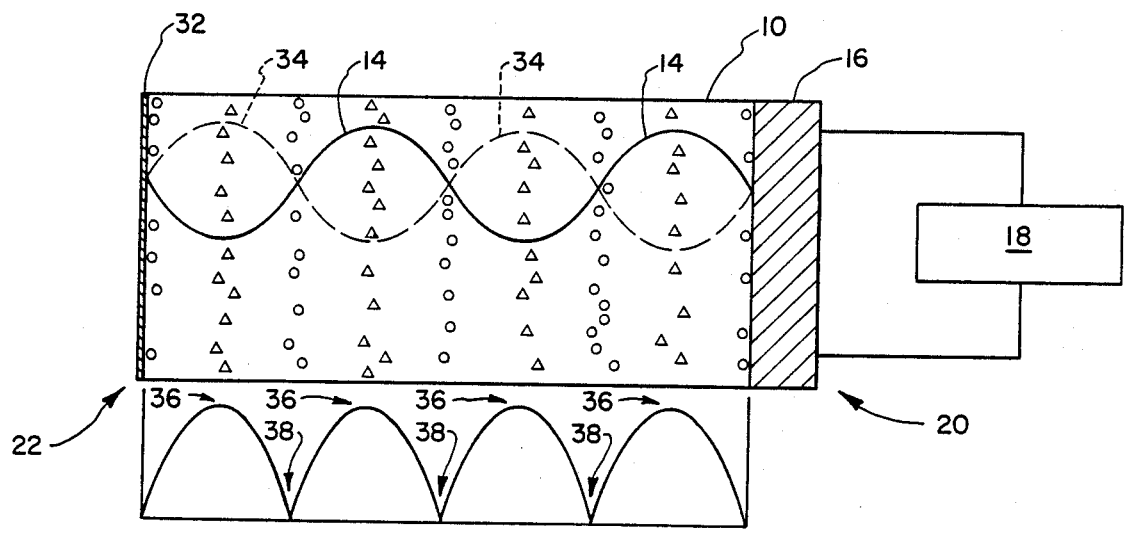
FIG. 2 is another representation of the system shown in FIG. 1 showing two acoustic pressure waves superimposed upon one another showing the regions of maximum and minimum pressure.

Reference will now be made to FIG. 2. In FIG. 2, system length 30 is the same as in FIG. 1. At the second end 22 of the system 10 is placed a surface 32 which reflects a high percentage of acoustic pressure wave 14 incident upon it. Since the length of the system 10 is an even multiple of wavelengths long, the reflected wave, shown by dashed sine wave 34, interferes with incident wave 14 to create a standing wave.

FIG. 2 shows reflected wave 34, superimposed upon incident wave 14. By creating a standing wave, areas of maximum pressure, commonly referred to as antinodes and generally designated 36, and areas of minimum pressure, commonly referred to as nodes and generally designated 38, are formed. The graph located at the bottom of FIG. 2 represents the root mean square pressure distribution with system 10. The vertical axis represents pressure levels which correspond to the standing wave within system 10. The wave form on the graph represents the pressure gradients within the chamber. The pressure gradient representation shown in the graph will be used several times in the following description of the embodiments of the present invention, rather than the sine wave representation.

As shown in FIG. 2, denser particles 26 and lighter particles 28, which were scattered throughout system 10 in FIG. 1, migrate to nodes 38 and antinodes 36, respectively. Generally stated another way, the denser particles move to regions of pressure minima while lighter particles move to regions of pressure maxima, as shown by the graph. In this fashion, particles of dissimilar physical properties, such as particles of dissimilar densities, may be segregated from the medium whose density is intermediate between the densities of lighter and denser particles.

With the particles segregated as shown in FIG. 2, it is possible to separate the particles from the medium. Indeed, various attempts in the prior art have been made to do so by way of providing structures that cause the physical separation of the particles and the medium after the segregation shown in FIG. 2 has occurred.

Unfortunately, such methods of physical separation as shown in the prior art do not lend themselves to allowing significant volumes of media to be quickly processed. However, the discussion that follows will explain how the present invention allows for extremely efficient aggregation and separation of particles from a medium.

The regions between the nodes and antinodes may best be described as pressure gradients, i.e., areas in which the pressure changes over a specified distance. In the standing wave, as shown in FIG. 2, the pressure gradients shown in the graph do not move. These stationary pressure gradients are an inherent characteristic of a standing wave. The present invention, while not using standing waves, uses a similar and related phenomenon, as well as exploiting additional principles, to move, aggregate, and separate particles from the medium as will now be explained.

Figure 3:
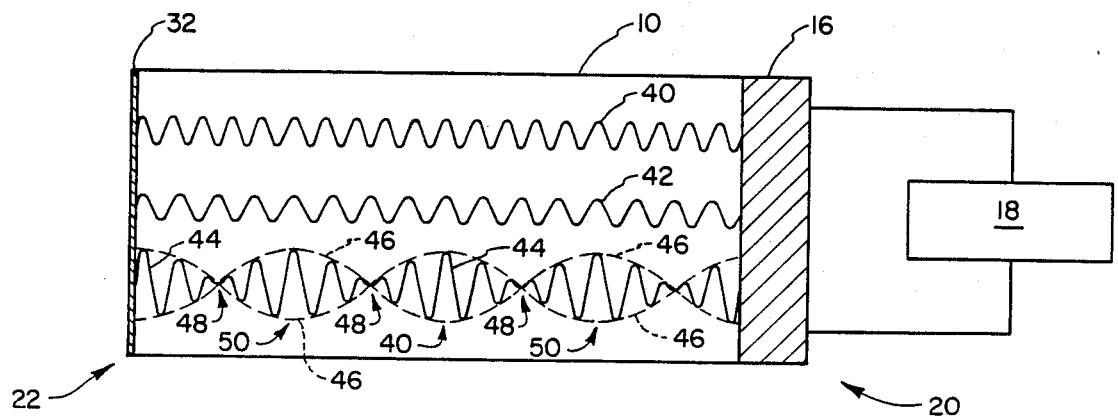
FIG. 3 is a further representation of the system shown in FIG. 2 showing two acoustic pressure waves of differing frequencies being propagated therethrough.

In FIG. 3, incident acoustic pressure wave 40, created by transducer 16 is of a first frequency. The reflected wave 42 has been altered so that its frequency, a second frequency, is slightly different than the first frequency. Methods in which the frequency of the reflected wave may be slightly shifted from the frequency of the incident wave will be explained later in this disclosure. For the present, this analysis assumes that the reflected wave has been shifted in frequency. When the two waves are superimposed, as shown in system 10, a beat frequency wave 44 may be observed as shown in FIG. 3.

As can be seen by the representation in FIG. 3, the resultant beat frequency is expressed by Equation B:

$$F_{Beat} = \frac{F_{inc} + F_{ref}}{2} \quad \text{(B)}$$

Where:
$F_{Beat}$ = Frequency of the Beat Wave
$F_{inc}$ = Frequency of the Incident Wave
$F_{ref}$ = Frequency of the Reflected Wave As shown by the dashed line outlining what is termed the envelope of beat frequency 46, the envelope of the beat frequency forms a wave pattern similar to that as with a standing wave. As explained in connection with FIG. 2, it must be appreciated that envelope 46 of the beat frequency represents areas of decreased and increased pressure in the medium as represented in dashed box 24 of FIG. 1. Furthermore, as mentioned in connection with the analysis of the standing wave, the beat frequency must actually be thought of as plane wave whose pressure gradients propagate through the medium parallel to the face of transducer 16. For ease of reference, and for clarity, the beat frequency wave form 46, as shown in FIG. 3, is hereinafter sometimes referred to as a "pseudo-standing wave."

The term "pseudo-standing wave" is adopted because of the similarity between the wave form of the envelope of the beat frequency wave and wave form of the "true" standing wave. Likewise, the node and antinode regions of the pseudo-standing wave envelope are termed "pseudo-nodes" and "pseudo-antinodes," as generally indicated at 48 and 50 in FIG. 3, respectively.

Figure 4:
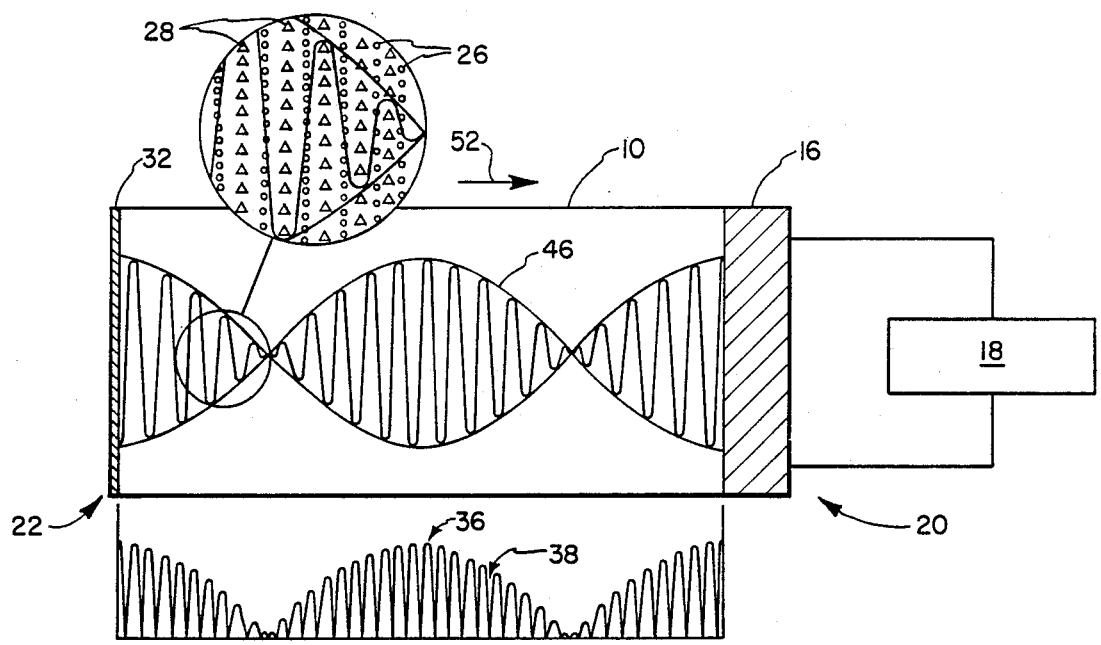
FIG. 4 is a further representation of the system and the acoustic pressure waves shown in FIG. 3, wherein the acoustic pressure waves are shown in greater detail.

It should be appreciated that even though FIG. 3, as well as FIG. 4, show that system 10 is resonant at all the wavelengths represented, the present invention does not require that system 10 be resonant. In fact, the majority of the embodiments disclosed herein operate principally at frequencies which do not resonate when used with the embodiments illustrated herein.

Reference will now be made to FIG. 4 to explain how the present invention effects the movement of the particles. FIG. 4 shows a pseudo-standing wave 46. The wavelength of the acoustic pressure waves, (only one wavelength of the envelope of the beat wave is represented in the system 10 of FIG. 4) which are superimposed upon each other to form the pseudo-standing wave, are much shorter than those shown in FIGS. 1, 2, and 3. One portion of FIG. 4 shows the acoustic pressure wave in much greater detail. The root mean square pressure gradients formed by the superposition of the acoustic pressure waves is represented in the lower portion of FIG. 4, just as the pressure gradients are shown in the lower portion of FIG. 2.

The enlarged portion of FIG. 4 shows the pressure gradients, with their associated nodes 38 and antinodes 36, as discussed in connection with FIG. 2. Also, the enlarged portion of FIG. 4 shows denser particles 26 and lighter particles 28 having migrated to nodes 38 and antinodes 36, respectively.

As the particles segregate as shown in FIG. 4, at nodes 38 and antinodes 36 of the pressure gradients, the segregated particles move as a group in the direction indicated by arrow 52. This is due to the fact that pseudo-standing wave 46 moves through time and space. Stated another way, the pressure gradients shown in the enlarged portion of FIG. 4, if viewed in real time, would appear to move in the direction indicated by arrow 52.

Furthermore, it is not necessary that a pressure gradient move only in the direction indicated by arrow 52. It is possible to cause the pressure gradients to move in the opposite direction to that shown by arrow 52. How this is accomplished will become clearer later in this description.

The movement and velocity of the pressure gradients of the acoustic pressure wave is termed the "group velocity," which will be mathematically described later in this description. It will be appreciated that, even though for simplicity of analysis, the preceding discussion refers to the migration or movement of particles to nodes 38 and antinodes 36, such migration or movement is not required by the present invention to separate the particles, as contrasted by some schemes presented in the prior art. However, if movement of the particles is all that is desired, such as when particles are being agitated or circulated in a liquid, movement of the particles to nodes 38 and antinodes 36 is not required, but only that the particles make some motion towards the pressure minima or pressure maxima.

Also, since nodes 38 and antinodes 36 merely represent the minima and maxima of the pressure gradients which move through space and time, as explained above, there is no need for "waiting" for particles 26 and 28 to migrate to nodes 38 and antinodes 36, but the moving pressure gradients will move towards a particle and "collect" it into a node or antinode. This phenomenon causes particles 26 and 28 to be moved or "swept" along until they are halted in their motion by a structure or until the acoustic pressure wave dissipates.

While the above description generally explains the methods of the present invention, it will also be appreciated that additional forces such as the Stokes viscous drag force and the Bjerkness force, may effect the movement of the particles. For example, the Stokes viscous drag force effects the available choices for a group velocity. If the group velocity is too fast, the pressure exerted on the particles by the pressure gradients will not overcome the Stokes force and no, or very little, particle movement will result. Alternatively, the group velocity must be fast enough so that the movement of the particles occurs in a reasonable period of time.

The Stokes force may be utilized to assist the separation process. The action of the moving pressure gradients on a particle is an exponential function related to the radius of the particle. The Stokes force is a linear function. Thus, because of the Stokes force, two particles possessing, for example, the same density, but of different radii, will generally be subject to different forces if acted upon by the same pressure gradients in the same medium. Making use of this characteristic, it is possible to effectuate the separation of particles from each other when the particles only differ in the volume that they occupy.

As the action of the pressure gradients upon the particles continues, particles 26 and 28 will be swept in direction 52 until they strike the exposed transducer face 56 where they will aggregate. It will be appreciated that the separation of particles 26 and 28 from the medium is greatly simplified using the above-described procedure as compared to methods used in the prior art wherein the particles were left in the arrangement as shown in FIG. 2 above.

An important consideration in the method of the present invention is the avoidance of cavitation in the propagating material or in the medium. As mentioned earlier, cavitation is the creation of disturbances in the medium due to the formation of gas bubbles caused by the application of acoustic pressure waves. It will be appreciated that cavitation in either the propagating material or the medium is counter productive to the objective of the present invention. Cavitation in either the the propagating material or medium disrupts the propagation of acoustic pressure waves as well as causing turbulence within the medium, thus being counter productive to any segregation or aggregation which has taken place in the medium.

Figure 5:
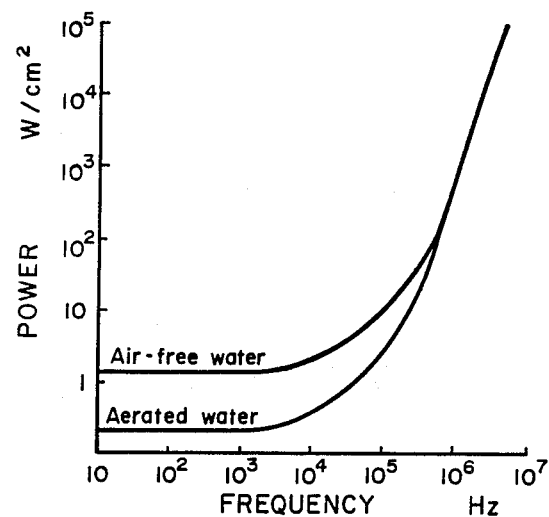
FIG. 5 is a graph generally describing one of the effects of acoustic pressure waves on water.

Since the majority of the applications of the presently preferred embodiments of the present invention deal with propagating materials and mediums which are mainly water, FIG. 5 has been included so as to indicate the approximate cavitation threshold of water. It will be appreciated that similar cavitation thresholds may be obtained for different propagating materials and media.

As can be seen from the chart of FIG. 5, gas-free water exhibits a cavitation threshold generally higher than, at least at frequencies below 1 mHz, aerated water. Since the introduction of cavitation is counter productive to the method of the present invention, a frequency and power level must be chosen so as to avoid the introduction of cavitation. Choosing frequencies and power levels well below the thresholds indicated in FIG. 5 are preferred.

An additional concern when choosing an operating frequency and power level, however, must be avoiding damage to, or the destruction of, the materials to be separated. This concern is especially applicable when subjecting biological materials to the method of the present invention. Damage to biological materials may be caused by physical deformation, increased temperatures, or several other possible effects of ultrasonic acoustic pressure waves. Generally, frequencies in the range of from about 1 mHz to about 10 mHz may be used in the present invention, however, for most applications frequencies in the range from about 2 mHz to about 3 mHz are preferred.

Having explained the fundamental principles which allow the present invention to operate so efficiently, several representative examples of the specific embodiments in which the present invention is incorporated, and examples of their use, will be explained.

C. Variable Frequency Transducer Embodiment

Figure 6:
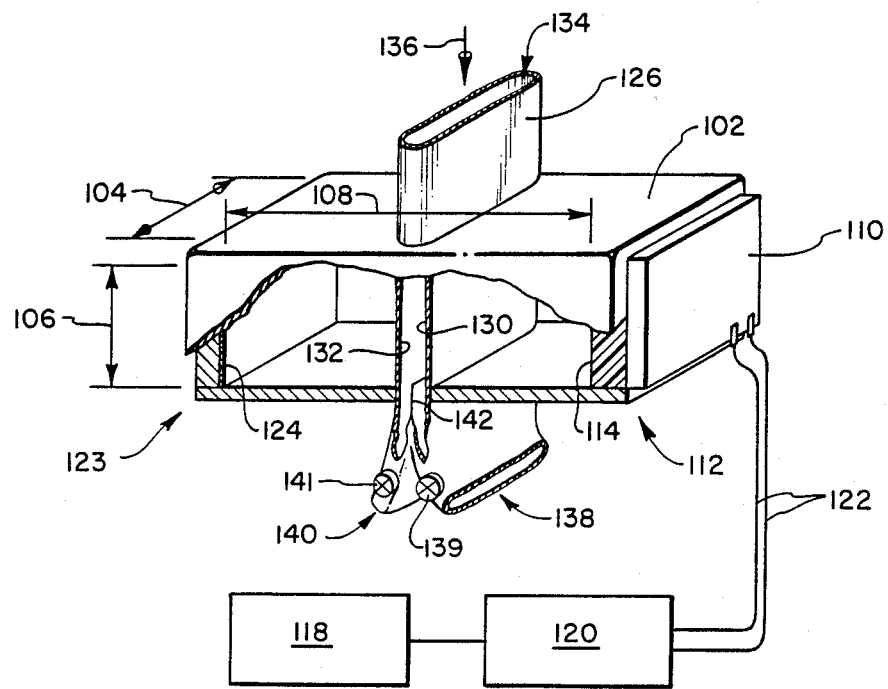
FIG. 6 is a perspective view of one presently preferred embodiment of the present invention.

The variable frequency transducer embodiment of the present invention is shown in the perspective view of FIG. 6. The embodiment illustrated in FIG. 6 generally comprises a propagation chamber 102. The interior dimensions of the chamber, which must be considered in the present invention, are its width, designated by line 104, its height, designated by line 106, and its length, designated by line 108 in FIG. 6.

Length 108 of propagation chamber 102, while not critical to the present invention, must be within reasonable limits in the present embodiment. The reason the length is not critical in the embodiment illustrated in FIG. 6 is that the embodiment is not intended to operate in a resonant mode, that is, the embodiment is not intended to create standing waves.

However, the fact that the embodiment illustrated in FIG. 6 will operate through a range of frequencies which may include a frequency which will resonate at the length of propagation chamber 102 that is chosen, requires that transducer 110 used to create the acoustic pressure waves be capable of providing a range of acoustic power to propagation chamber 102. This is because transducer 110 will "see" the acoustic impedance of the chamber change as the input frequency changes.

Later in this disclosure embodiments will be described using the present invention which overcome the requirement of using broad range transducers, which are characteristically less efficient, i.e., less acoustic output power per unit of electrical input power, than transducers which have an output variable over a very limited range of frequencies. The transducer as used in the embodiment illustrated in FIG. 6, and the embodiments illustrated in FIGS. 7-10, is preferably a piezoelectric transducer 10. However, other types of transducers could be used.

Height 106 of propagation chamber 102 shown in FIG. 6, is dependent upon the length of time that the particulate and medium mixture are to be subjected to ultrasonic treatment. If the height 106 of propagation chamber 102 is increased, then the particle and medium mixture may be subjected to the action of the ultrasonic waves for a longer period of time, even though the feed flow rate remains constant. This period of time is termed the "time in residence" or "residence time."

Generally, the longer the residence time, the greater the likelihood that complete aggregation and separation will occur. However, extending residence time indefinitely is not practical, and a balance must be struck between obtaining practical residence time durations and obtaining the desired separation. Other means of varying the residence time will be explained later.

Width 104 of propagation chamber 102, as well as height 106, are limited by the dimensions of available transducers suitable for use with the embodiment. Since a wave front is preferably to be propagated as a plane wave through propagation chamber 102 (that is, the wave front ideally should present equal pressure at all points in any plane which is parallel to the ends of chamber 102) transducer 110 must be of a size so as to create a uniform pressure wave across the width of propagation chamber 102.

Alternatively, a transducer which is not capable of producing a uniform plane wave may be used with a corresponding reduction in efficiency. However, multiple transducers could be mounted so as to present a single transmitting surface, with all of the transducers driven in phase, if greater transducer surface area were desired to increase residence time.

Transducer 110 is mounted onto propagation chamber 102 at a first end 112. A quarter wave acoustic impedance matching section 114 is disposed between transducer 110 and propagation chamber 102. Impedance matching section 114 acts to match the impedance of transducer 110 to the propagating material, generally designated 116, contained within the chamber 102. While impedance matching section 114 is not required in the embodiment shown in FIG. 6, the operation of transducer 110 may in some cases be improved if impedance matching section 114 is used. Impedance matching sections may also be used with the other embodiments described herein.

The propagating material of the embodiment illustrated in FIG. 6 is water. However, other propagating materials, such as oils, glass, or alcohol, could be used as particular conditions require. It will be appreciated that the propagation material acoustic impedance will preferably match the impedance of the medium and the structure containing the medium for maximum efficiency. However, an exact match is not required. The important property of propagating material 116 is that the acoustic pressure waves created by transducer 110 and coupled to propagating material 116 by impedance matching section 114 be carried accurately by the propagating material and that little cavitation will be induced.

In the embodiment illustrated in FIG. 6, the transducer is excited by variable frequency generator 118 whose signal is amplified to the necessary power levels by power amplifier 120. The particular frequencies used and the operation of the generator, transducer, and the embodiment illustrated in FIG. 6, will be explained later in this section. Wires 122 carry the electrical signal to transducer 110.

At a second end 123 of propagation chamber 102 is placed a reflector 124. The reflector is constructed so as to absorb very little of the incident acoustic pressure wave. For example, where a zinc reflector is used, it will reflect about 97% of the sound pressure wave incident upon it. Reflector 124 is precisely constructed so that the reflected wave is propagated back in the direction of the incident wave.

In the embodiment shown in FIG. 6, a separation vessel 126 is inserted through propagation chamber 102. Separation vessel 126 preferably extends the entire width, along line 104, of propagation chamber 102, and divides propagation chamber 102 into two separate cavities. In the illustrated embodiment, it is preferable that the separation vessel be located about halfway between the ends of propagation chamber 102. However, separation vessel 126 may be located either closer to propagation chamber first end 112 or second end 123 if desired as will become clear later.

The walls 130 and 132 of separation vessel 102 should be impermeable to the propagating material and medium, but transparent to the acoustic pressure waves traveling through propagation chamber 102 at the frequencies at which transducer 110 is operated. A medium and particle mixture is introduced into separation vessel 126 at a first end 134 of separation chamber 126, as indicated by arrow 136.

The mixture is introduced into separation vessel 126 at a predetermined flow rate. Since the flow rate partially determines the residence time, the flow rate is one factor which determines the percentage of separation which will be achieved using the embodiments of the present invention illustrated in the figures.

When separation vessel 126 is filled with a mixture of medium and particles, acoustic pressure waves created by transducer 110 will travel from propagation chamber first end 112 through separation vessel wall 130 and the medium, through separation chamber wall 132 to reflector 124. Separation chamber walls 130 and 132, while transparent to the acoustic pressure waves transmitted by transducer 110, are rigid such that the pressure of the medium and particle mixture being introduced into separation vessel 126 does not cause any significant deformation of separation chamber walls 130 and 132. Preferably, separation chamber walls 130 and 132 are both uniformly parallel to the face of transducer 110.

As will be explained shortly, when in operation, the particles contained in the mixture are moved adjacent to one wall of separation chamber 126. For example, in the embodiment illustrated in FIG. 6, the particles are moved adjacent to wall 130. As particles are aggregated next to wall 130, the medium, without particles, is displaced so as to be adjacent the opposite wall 132. As additional particle and medium mixture is moved into separation vessel 126, the particles and medium are separated as they are moved into separation collectors, generally designated 138 and 140.

As can be seen from the perspective view of FIG. 6, separation collectors 138 and 140 are joined at the point marked 142 called a separation surface. Separation surface 142 is preferably constructed so that the particles in the medium are separated without causing excessive turbulence in either the particles or the medium. The introduction of excessive turbulence is counter productive to the separation process since turbulence may cause the particles to be remixed with the medium. Furthermore, the flow rate into separation vessel 126 must also be chosen so as to avoid excessive turbulence.

As will be appreciated by an understanding of the operation of the embodiment, the distance between separation surface 142 and separation vessel walls 130 and 132 may be varied according to what particles and medium are to be separated and according to the degree of separation desired For example, if it is desired to remove particulate matter from water in order to provide particulate-free water, separation surface 142 may be positioned between separation vessel walls 130 and 132 such that the bulk of the particulate matter enters separation collector 138.

By moving separation surface 142 closer to separation vessel wall 130, the percentage of particles removed may be reduced. However, by making this adjustment, the percentage of water diverted to separation collector 138 will also be reduced. Thus, the position of separation surface may be altered according to the particular application of the embodiment.

Still further, it will be appreciated that the percentage of separation may be varied by altering the feed flow rate through separation vessel 126. Furthermore, the percentage of separation may also be varied by including valves, shown schematically at 139 and 141 in FIG. 6, in the flow paths of separation collectors 138 and 140, respectively. As valves 139 and 141 are opened, it will be seen that the residence time will be decreased and when valves 139 and 141 are closed some what, the opposite effect will be seen. Adjusting the positions of valves 139 and 141 has an effect similar to moving the orientation of separation surface 142. Thus, the percentage of separation may be altered by adjusting valves 139 and 141.

Furthermore, it will be appreciated that the use of separation vessel 126, which prevents contact between the medium and the propagation material, not only assists with the aggregation and separation process, as will be explained later, but also facilitates the convenient use of the embodiment in many applications.

For example, as will be discussed later, the illustrated embodiment has valuable application for separation of blood cells from plasma. Since separation vessel 126 may be constructed so as to be easily replaced, the need for sterilizing the complete embodiment is avoided since separation vessel 126 may be disposable.

Figure 7:
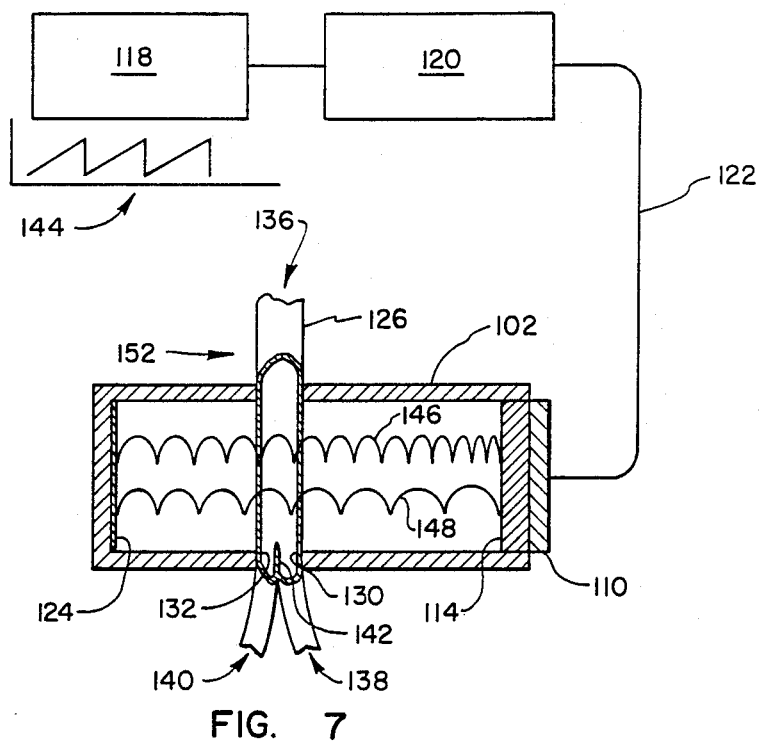
FIG. 7 is an elevated cross-sectional view of the embodiment shown in FIG. 6.

Reference will now be made to FIG. 7 in order to further explain the operation of the embodiment shown in FIG. 6. FIG. 7 is an elevated cross-sectional view of the embodiment illustrated in FIG. 6.

The pseudo-standing wave referred to in connection with FIGS. 3 and 4 above, may be created in the embodiment shown in FIG. 7, as explained below. Variable frequency generator 118 is operated so as to create a wave form whose frequency increases as time passes. The ramp wave form, generally designated 144 in FIG. 7, generally indicates the function used by variable frequency generator 118 to increase the frequency over time between two values and then to return rapidly to the lowest frequency.

Alternatively, a variable frequency generator may be structured so as to create a wave form whose frequency decreases with time. The case in which the frequency increases with time will be used to explain the operation of the embodiment illustrated in the figures; however, it will be understood that if the frequency is decreased over time, the effect of the pressure waves within propagation chamber 102 and separation vessel 126 will be the same with only the direction of movement being reversed. Furthermore, it is to be understood that ramp wave form 144 is merely representative of the wave forms which may be used. For example, the wave form could be the linear wave form shown, an exponential wave form, or could follow some other function depending on the particular application of the embodiment.

With variable frequency generator 118 creating a wave form which increases with frequency as time passes, transducer 110 will create a corresponding wave form in the propagation material. Thus, as the wave form propagates through propagation chamber 102, the wavelengths of the pressure waves found nearest reflector 124 will be longer than the wavelength of the pressure waves nearest transducer 110.

This is shown schematically by the pressure gradient wave form labeled 146 in FIG. 7, which is exaggerated to show the effect of "ramping" the frequency generator 118. Since the frequency found at the face of transducer 110 has been "ramping" upward, the wave reflected from reflector 124, represented by the pressure gradient wave form marked 148, will be decreasing in frequency, relative to incident wave 146 as it approaches transducer 110.

Since propagation chamber 102 may be only several wavelengths long, and frequency generator is ramping upward in frequency only a small amount, for example as little as about 0.0001%, during the time it takes pressure waves to traverse propagation chamber 102 twice, the difference in frequency between the acoustic pressure waves at any particular two points within propagation chamber 102 will only be slight and will create a beat wave whose envelope is of low frequency, or in other words, a "pseudo-standing wave". It should be noted that the pressure gradient wave forms shown in FIG. 7, representing incident wave 146 and reflected wave 148, are not to scale and have been exaggerated to demonstrate the concept that the frequencies of the two waves differ.

The frequency difference between the incident wave 146 and the reflected wave 148 will be zero at the surface of reflector 124 and will be greatest at the face of transducer 110 The reflected wave 148 superimposed upon the incident wave 146 creates the pseudo-standing wave.

The pseudo-standing wave which has been created as described above moves through space and time within s propagation chamber as explained in connection with FIG. 5 above. The velocity of the pressure gradients the pseudo-standing wave is termed the group velocity. Thus, the pressure gradients of the pseudo-standing wave move as described in connection with the pseudo-standing wave illustrated in FIG. 4. The particles contained in the medium are carried along with the moving pressure gradients in the direction of arrow 152.

However, due to the fact that the movement of particles is restricted by separation vessel wall 130, the particles are aggregated adjacent to separation vessel wall 130. The creation of pseudo-standing waves, whose movement is described by the group velocity equation to be provided later, cause the segregation of particles and medium within separation vessel 126 as shown in detail in FIG. 7A.

Figure 7A:
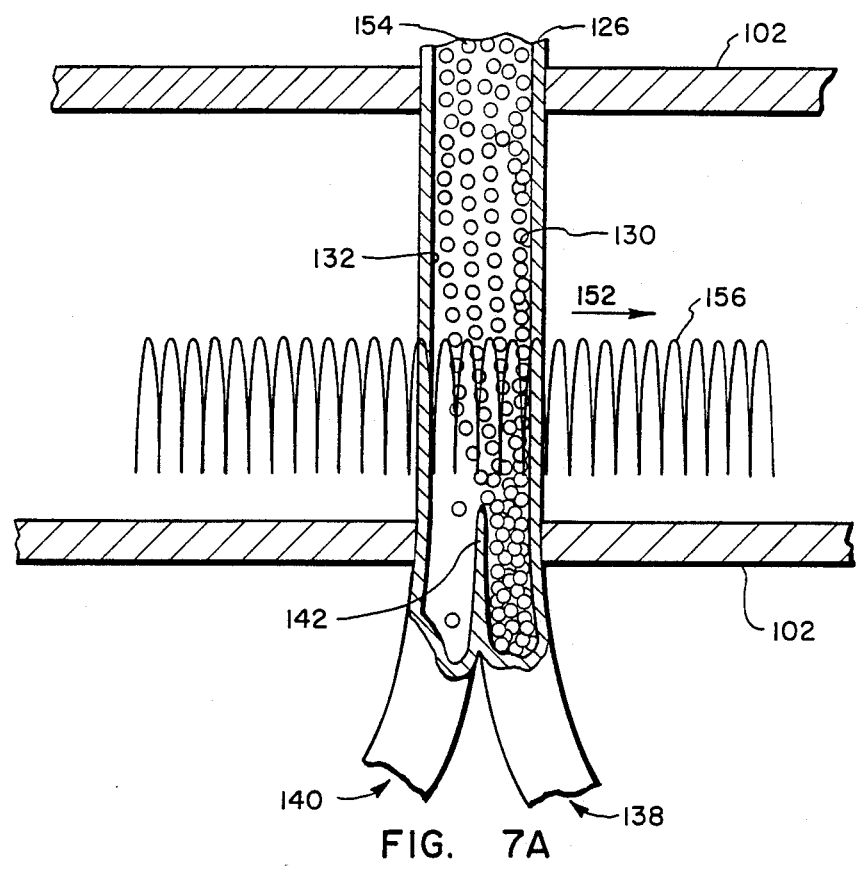
FIG. 7A is an elevated cross-sectional view showing a portion of the embodiment shown in FIG. 7.

FIG. 7A is an elevated cross-sectional view of separation chamber 126 along a section through which the vessel traverses propagation chamber 102. In FIG. 7A, blood cells, represented by the objects marked 154, are shown being fed into separation vessel 126 in the direction indicated by arrow 130.

As blood cells 154 and plasma mixture enter separation vessel 126, blood cells 154 are uniformly dispersed throughout the plasma. As blood cells 154 continue to travel through separation vessel 126, they are acted upon by pressure gradients 156, moving in the direction shown by arrow 152.

The action of pressure gradients 156 cause blood cells 154 to aggregate in the regions of pressure minima. Since the pressure gradients 156 are moving, the blood cells aggregate along separation vessel wall 130. With a high percentage of blood cells 154 aggregated along wall 130, blood cells 154 may be separated from the plasma by directing blood cells 154 through separation collector 138.

As will be appreciated, the embodiment may be used to separate many different materials having different physical properties, not just blood cells from plasma. It should also be appreciated that altering the feed flow rate into separation vessel 126, the length of separation vessel 126, the position of separation surface 142, and the orientation of valves 139 and 141, all will affect the percentage of separation. Furthermore, the particular frequencies used, the rate of change of the frequencies (i.e., the ramp rate), the width of the separation chamber, and additional factors, must be considered when using the embodiments illustrated in the figures.

The creation of a pseudo-standing wave and its associated group velocity (i.e., the velocity of the pressure gradients of the pseudo-standing wave), may be described mathematically. As explained above the difference in frequency between the incident and reflected acoustic pressure waves will be at a minimum at the surface of reflector 124 and at a maximum at the point at which the acoustic pressure wave is transmitted into the propagation material, i.e., the surface of impedance matching section 114, as shown in FIG. 7A. This result is caused by the fact that the reflected wave will have traveled the maximum distance possible once it has reached the first end of propagation chamber as well as the fact that the reflected wave will have the maximum difference in frequency from the acoustic pressure wave currently being propagated by transducer 110 due to the ramp function of variable frequency generator 110.

Choosing a locus ("z") somewhere within the propagation chamber with the reflector surface being defined as the starting point where z=0 and where L equals the length of the propagation chamber, the group velocity (sometimes also referred to as the beat velocity) may be determined by defining the ramp rate. The ramp rate is the rate of change of the transducer frequency and is expressed by Equations $C_1$ and $C_2$:

$$\omega_{inc} = \omega_o - R\left(\frac{L+z}{c}\right) \quad (C_1)$$

$$\omega_{ref} = \omega_o - R\left(\frac{L-z}{c}\right) \quad (C_2)$$

Where:
$\omega_o$ = instantaneous frequency of transducer
$R$ = ramp rate
$\omega_{inc} > \omega_{ref}$ at z, ie., a positive or upward ramp Having defined the ramp rate, the group velocity may be determined by Equation D:

$$V_g = \frac{c(\omega_{ref} - \omega_{inc})}{\omega_{ref} + \omega_{inc}} c = -\frac{Rzc}{\omega_o c - RL} \quad (D)$$

Where:
$V_g$ = group velocity

The ramp rate, R, may be either positive or negative. As generally explained earlier, the group velocity describes the movement of the nodes and antinodes, and thus the pressure gradients, of the pseudo-standing wave. Thus, the group velocity also describes the general movement of the particles which have been aggregated at pressure minima by the action of the moving pressure gradients. The particles will, in many cases, move with their corresponding band.

It will be appreciated that in practice not all of the particles will acquire the same velocity as the group velocity In the present invention, each particle may be acted upon by a plurality of pressure gradients, since, at the frequencies used, many pressure gradients may have moved past each particle during its time in residence. Furthermore, it is not necessary that the particles migrate to a node or antinode, but only that the particles be acted upon by the moving pressure gradients sufficiently to overcome the drag forces present and cause the particles to move a very short distance. The maximum lateral distance each particle is required to move is equal to the distance between separation vessel walls 130 and 132.

Figure 7B:
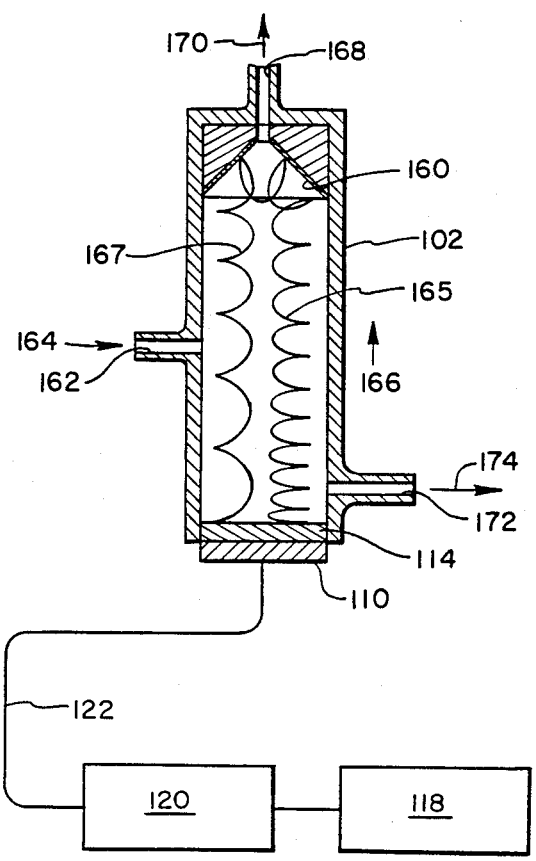
FIG. 7B is an elevated cross-sectional view of another embodiment of the present invention.

Another embodiment using the variable frequency generator is shown in FIG. 7B. FIG. 7B is an elevated cross-section of the retro-reflector embodiment of the present invention illustrating the pressure amplitude of a single wave transmitted by the transducer and reflected by the retro-reflector surface. It is to be understood that the pressure wave is transmitted as a plane wave across the entire transducer surface. Similar to the variable frequency embodiment shown in FIG. 7, the retro-reflector embodiment uses a variable frequency generator 118, power amplifier 120, and transducer 110 which is coupled to the propagation material contained in propagation chamber 102 by quarter-wave impedance matching section 114.

The retro-reflector embodiment shown in FIG. 7B has two significant differences from the variable frequency embodiment shown in FIG. 7, as will be pointed out. First, reflector surface 160 is preferably formed in a conical shape having a 90° apex. The conical shape causes acoustic pressure waves to be reflected laterally across the axis of the chamber and then reflected in the opposite direction. Second, the retro-reflector embodiment does not require a separation vessel since the particle and medium mixture is introduced directly into the propagation chamber 102.

Shapes other than the conical shape represented in FIG. 7B may be used for reflector surface 160; the important factor is that the reflector surfaces are oriented at 90° in relation to the opposite reflecting surface. For example, a pyramid shape may be used if its apex forms a 90° angle.

The particle and medium mixture is introduced into propagation chamber 102 through feed passage 162 in the direction indicated by arrow 164. As the particles enter propagation chamber 102 they are acted upon by the pressure gradients of the beat wave formed by superposition of the reflected waves upon the incident waves from the transducer. This results in pseudo-standing waves possessing a group velocity as explained earlier. Due to the group velocity of the pseudo-standing waves, the particles are urged to move in the direction indicated by arrow 166. The incident wave pressure gradients are marked 165 while the reflected wave pressure gradients are marked 167.

The number of segregated particles per unit volume increases as reflector surface 160 is approached. Due to the 90° reflection at the retro-reflector, the particles will be urged into annular pressure minima surrounding the axis of the cone. The particles are eventually aggregated into a central rod, which subsequently exits the device through a first discharge passage 168 in the direction indicated by arrow 170. The particle free medium leaves propagation chamber 102 through a second discharge passage 172, in the direction of arrow 174, as additional particle and medium mixture is forced into propagation chamber 102 through feed passage 162.

Below are given several examples showing the effectiveness of the variable frequency embodiment illustrated in FIGS. 6, 7 and 7B.

EXAMPLE 1

An embodiment within the scope of the present invention and substantially similar to that shown in FIG. 7 above was used in order to separate red blood cells from plasma. The dimensions of the structures used in this example have the following values:

Dimensions of the propagation chamber:
Height=2.5 centimeters (cm)
Width=2.5 cm
Length=7.5 cm
Dimensions of the separation vessel:
Width=6 millimeters (mm)
Residence length=2.5 cm
Distance from propagation chamber ends=3.25 cm
Separation surface orientation: centered
Separation vessel material: urethane rubber The frequency generator used in this example was manufactured by Exact Electronics, Inc., model no. 528; the power amplifier was manufactured by Electronic Navigation Industries, Inc., model no. 240L RF Power Amplifier; the transducer material was composed of lead zirconate titanate (PZT-4); and, the reflector material was aluminum.

The method of the present invention was operated utilizing the following parameters:
Transducer frequency=2.2 mHz
Ramp rate=10 kHz/second
Ramp direction: Upward
Cycle time for ramp=10 seconds
Input power=50 watts peak
Output power=5 watts/cm$^2$
Input feed flow=2 milliliters (ml)/minute (min)

The original blood cell percentage in the plasma was about 26% in the continuous flow stream. However, analysis of the products separated according to the procedures of this example showed that there was less than about 0.5% of the blood cells remaining in the plasma.

EXAMPLE 2

A process within the scope of the present invention was conducted in order to separate red blood cells from plasma. The conditions, structures, parameters, and process were the same as in Example 1, except that the transducer frequency was 3.2 mHz, the ramp rate was 8 kHz/second, and the power input was 40 watts peak.

The original red blood cell percentage in the plasma was about 26% in the continuous fluid stream. However, analysis of the products separated according to the procedures of this example showed that there was less than about 1% of the red blood cells remaining in the plasma.

EXAMPLE 3

A process within the scope of the present invention was conducted in order to separate red blood cells from plasma. The conditions, structures, parameters, and process were the same as in Example 1, except that the transducer frequency was 2.0 mHz, the input power was 60 watts peak, and the output power was 6 watts/cm$^2$.

The original percentage of red blood cells in the plasma was about 35% in the continuous fluid stream. However, analysis of the products separated according to the procedures of this example showed that there was less than about 6% of the red blood cells remaining in the plasma.

EXAMPLE 4

A process within the scope of the present invention is conducted using an embodiment substantially similar to that shown in FIG. 7B above for the purpose of separating gas bubbles from water. The bubbles are dispersed into the water to provide bubbles ranging in size from about 10 to about 100 microns. The dimensions of the structures for this example have the following values:

Dimensions of the propagation chamber:
Height=2.5 cm
Width=2.5 cm
Length=2.5 cm

The frequency generator used in this example is manufactured by Exact Electronics, Inc., model no. 528; the power amplifier is manufactured by Electronic Navigation Industries, Inc., model no. 240L RF Power Amplifier; the transducer material is composed of lead zirconate titanate (PZT-4); the impedance matching section is made of boron nitride; and, the reflector material is aluminum formed in a 90° cone.

The method of the present invention is operated utilizing the following parameters:

Transducer frequency=2.2 mHz
Ramp rate=10 kHz
Ramp direction: upward
Cycle time for ramp=10 seconds
Input power=50 watts peak
Output power=5 watts/$cm^2$
Input feed flow=6 ml/min Utilizing the procedures of to this example, good separation of the bubbles from the water is visually observable.

EXAMPLE 5

An embodiment within the scope of the present invention and substantially similar to that shown in FIG. 7B above was used for the purpose of separating a mixture of two immiscible liquids (oil and water). The oil was dispersed into the water to provide droplets ranging in size from about 1 to about 100 microns. The dimensions of the structures used in this example have the following values:

Dimensions of the propagation chamber:
Height=2.5 cm
Width=2.5 cm
Length=2.5 cm

The frequency generator used in this example was manufactured by Exact Electronics, Inc., model no. 528; the power amplifier was manufactured by Electronic Navigation Industries, Inc., model no. 240L RF Power Amplifier; the transducer material was composed of lead zirconate titanate (PZT-4); the impedance matching section was made of boron nitride; and, the reflector material was aluminum formed in a 90° cone.

The method of the present invention was operated utilizing the following parameters:

Transducer frequency=2.2 mHz
Ramp rate=10 kHz
Ramp direction: upward
Cycle time for ramp=10 seconds
Input power=50 watts peak
Output power=5 watts/$cm^2$
Input feed flow=6 ml/min
Output flow=1.2 ml/min for oil
Output flow=4.8 ml/min for water The original oil percentage in the water was about 22% in the continuous flow stream. However, analysis of the products separated according to the procedures this example showed that there was less than about 5% of the oil remaining in the water after passing through the separation chamber.

EXAMPLE 6

A process within the scope of the present invention was conducted in order to separate oil from water. The conditions, structures, parameters, and process were the same as in Example 5, except that the original oil concentration in the water was 5% with droplets ranging in size from about 1 to about 10 microns, the input feed flow was 4 ml/min, and the output flow was 0.5 ml/min for oil and 3.5 ml/min for water.

The original percentage in the water was about 5% in the continuous fluid stream. However, analysis of the products separated according to the procedures of this example showed that there was less than about 0.1% of the oil remaining in the water after through the separation chamber.

EXAMPLE 7

A process within the scope of the present invention was conducted in order to separate two immiscible liquids (Puritan ® brand salad oil and water). The conditions, structures, parameters, and process were the same as in Example 5, except that no impedance matching section was used.

The original oil percentage in the water was about 22% in the continuous fluid stream. However, analysis of the products separated according to the procedures of this example showed that there was less than about 1% of the oil remaining in the water after passing through the separation chamber.

EXAMPLE 8

An embodiment within the scope of the present invention and substantially similar to that shown in FIG. 7 above was used in order to separate polystyrene microspheres (having an average diameter of 30 microns) from water. The dimensions of the structures used in this example had the following values:

Dimensions of the propagation chamber:
Height=2.5 cm
Width=2.5 cm
Length=7.5 cm
Dimensions of the separation vessel:
Width=6 mn
Residence length=2.5 cm
Distance from propagation chamber ends=3.25 cm
Separation surface orientation: centered
Separation vessel material: urethane rubber The frequency generator used in this example was manufactured by Exact Electronics, Inc., model no. 528; the power amplifier was manufactured by Electronic Navigation Industries, Inc., model no. 240L RF Power Amplifier; the transducer material was lead zirconate titanate (PZT-4); and, the reflector material was aluminum.

The method of the present invention was operated utilizing the following parameters:

Transducer frequency=2 mHz
Ramp rate=10 kHz/sec
Ramp direction: Upward
Cycle time for ramp=10 sec
Input power=20 watts peak
Output power=2 watts/$cm^2$
Input feed flow=1.5 ml/min The original volume of microspheres in the water was about 1% in the continuous flow stream. However, analysis of the products separated according to the procedures of this example showed that there was less than about 0.1% of the microspheres remaining in the water after passing through the separation chamber.

EXAMPLE 9

A process within the scope of the present invention was conducted in order to separate polystyrene microspheres from water. The conditions, structures, parameters, and process were the same as in Example 8, except that the microspheres were 5 microns in diameter.

The original microsphere percentage in the water was about 1% in the continuous fluid stream. However, analysis of the products separated in this example showed that there was less than about 0.1% of the microspheres remaining in the water after passing through the separation chamber.

EXAMPLE 10

An embodiment within the scope of the present invention substantially similar to that shown in FIG. 7B above was used according to the present invention in order to separate polystyrene microspheres 34 microns in diameter from water. The dimensions of the structures used in this example have the following values:

Dimensions of the propagation chamber:
Height=2.5 cm
Width=2.5 cm
Length=7.5 cm

The frequency generator used in this example was manufactured by Exact Electronics, Inc., model no. 528; the power amplifier was manufactured by Electronic Navigation Industries, Inc., model no. 240L RF Power Amplifier; the transducer material was lead zirconate titanate (PZT-4); and, the reflector material was aluminum.

The method of the present invention was operated utilizing the following parameters:
Transducer frequency=2 mHz
Ramp rate=10 kHz/sec
Ramp direction: Upward
Cycle time for ramp=10 sec
Input power=20 watts peak
Output power=2 watts/cm$^2$
Input feed flow=1.5 ml/min The original volume of microspheres in the water was about 1% in the continuous flow stream. However, analysis of the products separated according to the procedures of this example showed that there was less than about 0.1% of the microspheres remaining in the water after passing through the separation chamber.

D. Moving Reflector Embodiment

Figure 8:
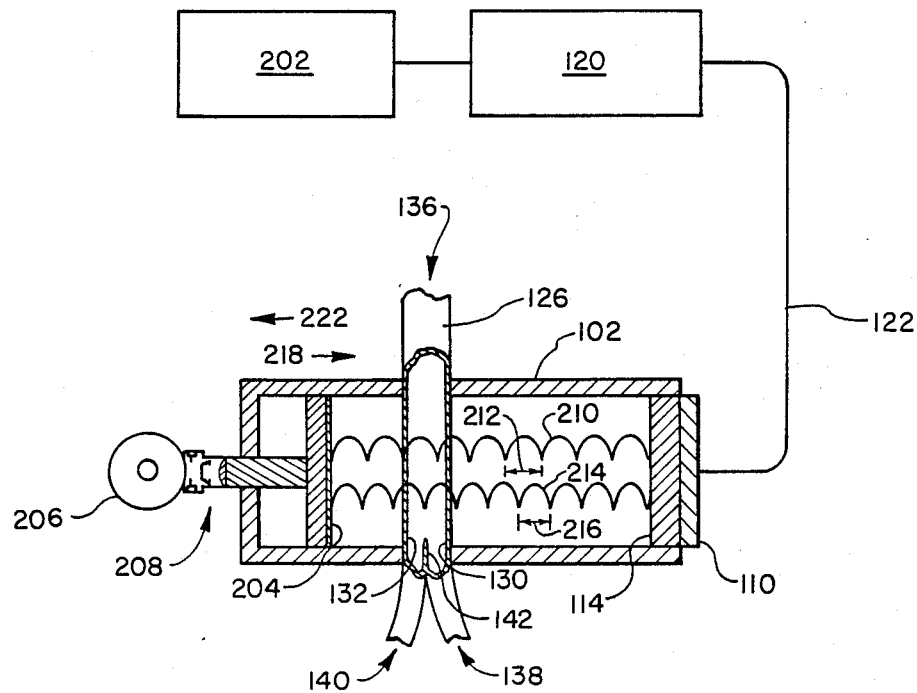
FIGS. 8-10 are elevated cross-sectional views of three other alternative embodiments of the present invention.

FIG. 8 is a cross-sectional view showing the structure of the moving reflector embodiment of the present invention. The structure of the moving reflector embodiment is similar to the structure of the variable frequency embodiment shown in FIGS. 6 and 7 with two significant alterations.

First, variable frequency generator 118, shown in FIGS. 6 and 7, has been replaced by a fixed frequency generator 202. Second, reflector 124, shown in FIGS. 6 and 7, has been replaced by a moving reflector 204 which is driven by a motor 206 and interconnecting linkage 208, such that the reflector is driven in a reciprocating piston-like fashion. In some applications it may be advantageous to incorporate a conical-shaped reflective surface, as described in connection with the retro-reflector embodiment shown in FIG. 7B, into moving reflector 204.

As is the case with the variable frequency transducer embodiment, shown in FIGS. 6, 7, and 7B, the objective of the embodiment shown in FIG. 8 is to produce pseudo-standing waves whose moving pressure gradients may be utilized to move particles to one side of separation vessel 126. In order to create a pseudo-standing wave having moving pressure gradients, it is necessary to propagate a reflected acoustic pressure wave possessing a different frequency than the incident acoustic pressure wave propagated by transducer 110.

With frequency generator 202 being fixed at a single frequency, moving reflector 204 allows the reflected wave to increase or decrease in frequency, as compared to the incident pressure wave, due to the well-known Doppler effect. The shift in frequency due to the Doppler effect, hereinafter called the "Doppler shift," causes the reflected wave to be shifted in frequency by an amount which is directly related to the velocity of moving reflector 204.

As shown in FIG. 8, incident wave 210 has a wavelength designated by 212, while the reflected wave 214 has a wavelength designated by 216. The reflected wavelength 216 is shorter than the incident wavelength 212 when moving reflector 204 travels in the direction marked by the arrow labeled 218.

Alternatively, when moving reflector 204 travels in the direction shown by arrow 222, the Doppler-shifted reflected wave 214 will have a shorter wavelength than incident wave 210. The Doppler-shifted reflected wave 210 superimposed upon the incident wave 214 creates a pseudo-standing wave. Furthermore, the group velocity (i.e., the velocity of the travel of the pressure gradients of the pseudo-standing wave) is linearly related to the velocity of moving reflector 204.

Thus, by incorporating a moving reflector 204 into the embodiment, pseudo-standing waves having moving pressure gradients may be created in propagation chamber 102 and transmitted through separation vessel 126, thereby causing the aggregation and separation of particles from the medium as shown in FIG. 7A. As is the case with the variable frequency embodiment shown in FIGS. 6 and 7 above, the particles may be caused to aggregate along either separation vessel wall 130 or separation vessel wall 132.

The travel of moving reflector 204 in the direction indicated by arrow 218 will cause the pressure gradients of the pseudo-standing waves to move in the direction indicated by arrow 218, thereby causing the particles to move in the same direction. When the direction of moving reflector 204 is reversed, as in the direction of arrow 222, the particles will similarly travel in the opposite direction. In order to avoid having a zero net movement of particles when using the moving reflector embodiment, it is necessary to prevent the movement of the particles while moving reflector is traveling to its initial position.

A first method of preventing movement of particles during one direction of moving reflector travel is to cause moving reflector 204 to move at two velocities: a first velocity termed a "Doppler velocity", and a second velocity termed a "return velocity." The Doppler velocity is the correct velocity which moving reflector 204 should travel in order to cause the correct Doppler shift in the reflected pressure wave 214.

The return velocity must be much greater than the Doppler velocity. The criteria for selecting the return velocity should be that the return velocity must be high enough that any movement in the pseudo-standing wave pressure gradients would be too rapid to be followed by the particles with their relatively high inertia and viscous drag.

A preferred method of eliminating the effect of moving reflector 204 traveling in both directions is to switch frequency generator 202 off during the period that moving reflector 204 is moving in the direction opposite to that desired for segregating particles. By switching off frequency generator 202 during the proper interval, motor 206 and linkage 208 may be allowed to operate continuously to provide the reciprocating motion.

As stated above, the movement of the pressure gradients of the pseudo-standing wave, and thus the movement of the particles, are linearly related to the movement of moving reflector 204. The linear relationship may be expressed by the equations as set forth below.

The Doppler shift introduced by moving reflector is expressed by Equation E:

$$\omega_{ref} = \omega_{inc} \frac{c + \mu}{c - \mu} \quad \text{(E)}$$

Where:
$\mu$ = Velocity of the moving reflector

The equation giving the Doppler shift of the reflected wave may be substituted into the group velocity equation, given above, to obtain Equation F:

$$V_g = \frac{c\left(\omega_o\left(\frac{c+\mu}{c-\mu}\right) - \omega_o\right)}{\omega_o + \left(\omega_o \frac{c+\mu}{c-\mu}\right)} = \mu \quad \text{(F)}$$

By properly choosing and controlling the frequencies generated by frequency generator 202 and appropriately 2. controlling the velocity of moving reflector 204, as shown in FIG. 8, the particles and medium may be separated from one another as described in connection with FIGS. 6, 7, and 7A, above. Examples of the moving reflector embodiment shown in FIG. 8 being used to separate various materials are given below.

EXAMPLE 11

An embodiment within the scope of the present invention and substantially similar to that shown in FIG. 8 above was used in order to separate blood cells from plasma. The dimensions of the structures used in this example have the following values:
Dimensions of the propagation chamber:
Height=2.5 cm
Width=2.5 cm
Length=5 cm
Dimensions of the separation vessel:
Width=6 mm
Residence length=2.5 cm
Distance from propagation chamber ends=2.5 cm
Separation surface orientation: centered
Separation vessel material: acrylic
The frequency generator used in this example was manufactured by Exact Electronics, Inc., model no. 528; the power amplifier was manufactured by Electronic Navigation Industries, Inc., model no. 240L RF Power Amplifier; the transducer material was lead zirconate titanate (PZT-8); the impedance matching section was made of glass; and, the reflector material was aluminum.

The method of the present invention was operated utilizing the following parameters:
Transducer frequency=5 mHz
Reflector velocity=0.1 mm/sec
Cycle time for reflector=10 sec
Input power=10 watts peak
Output power=10 watts/cm²
Input feed flow=6 ml/min The original blood cell percentage in the plasma was about 26% in the continuous flow stream. However, analysis of the products separated according to the procedures of this example showed that there was less than about 10% of the blood cells remaining in the plasma.

EXAMPLE 12

A process within the scope of the present invention is conducted in order to separate blood cells from plasma. The conditions, structure, parameters, and process are the same as in Example 11, except that the reflector velocity is 0.07 mm/sec, and the input feed flow is 4 ml/min.

According to the procedures of this example, excellent separation of the blood cells from the plasma is achieved.

EXAMPLE 13

A process within the scope of the present invention was conducted in order to separate blood cells from plasma. The conditions, structures, parameters, and process were the same as in Example 11, except that the transducer frequency was 2.2 mHz.

The original blood cell percentage in the plasma was about 26% in the continuous fluid stream. However, analysis of the products separated according to the procedures of this example showed that there was less than about 3% of the blood cells remaining in the plasma.

EXAMPLE 14

A process within the scope of the present invention is conducted using an embodiment substantially similar to that shown in FIG. 8 above in order to separate gas bubbles ranging in size from about 10 to about 100 microns from water. The dimensions of the structures used in this example have the following values:
Dimensions of the propagation chamber:
Height=2.5 cm
Width=2.5 cm
Length=5 cm
Dimensions of the separation vessel:
Width=6 mm
Residence length=2.5 cm
Distance from propagation chamber ends=2.5 cm
Separation surface orientation: centered
Separation vessel material: acrylic
The frequency generator used in this example is manufactured by Exact Electronics, Inc., model no. 528; the power amplifier is manufactured by Electronic Navigation Industries, Inc., model no. 240L RF Power Amplifier; the transducer material is PZT-4; the impedance matching section is made of boron nitride; and, the reflector material is aluminum.

The method of the present invention is operated utilizing the following parameters:
Transducer frequency=2.5 mHz
Reflector velocity=0.1 mm/sec
Cycle time for reflector=10 sec
Input power=50 watts peak
Output power=5 watts/cm²
Input feed flow=4 ml/min According to the procedures of this example, adequate separation of the bubbles from the water is achieved.

EXAMPLE 15

A process within the scope of the present invention is conducted using an embodiment substantially similar to that shown in FIG. 8 above for the purpose of separating crude oil dispersed in droplets ranging in size from about 1 to about 100 microns from water. The dimensions of the structures used for this example have the following values:

Dimensions of the propagation chamber:
    Height=2.5 cm
    Width=2.5 cm
    Length=5 cm
    Dimensions of the separation vessel:
    Width=6 mm
    Residence length=2.5 cm
    Distance from propagation chamber ends=2.5 cm
    Separation surface orientation: centered
    Separation vessel material: acrylic The frequency generator for this example is manufactured by Exact Electronics, Inc., model no. 528; and power amplifier is manufactured by Electronic Navigation Industries, Inc., model no. 240L RF Power Amplifier; the transducer material is PZT-4; the impedance matching section is made of boron nitride; and, the reflector material is aluminum.

The method of the present invention is operated utilizing the following parameters:

Transducer frequency=2.5 mHz
    Reflector velocity=0.1 mm/sec
    Cycle time for reflector=10 sec
    Input power=50 watts peak
    Output power=5 watts/cm$^2$
    Input feed flow=4 ml/min According to the procedures of this example, excellent separation of the oil from the water is achieved.

EXAMPLE 16

A process within the scope of the present invention is conducted for the purpose of separating oil from water. The conditions, structures, parameters, and process are the same as in Example 15, except that the transducer frequency is 2 mHz, the reflector velocity is 0.09 mm/min, the power input is 60 watts peak, the power output is 6 watts/cm$^2$, and the input flow rate is 3 ml/min.

According to the procedures of this example, excellent separation of the oil from the water is achieved.

EXAMPLE 17

An embodiment within the scope of the present invention and substantially similar to that shown in FIG. 8 above was used in order to separate polystyrene microspheres 34 microns in diameter from water. The dimensions of the structures used in this example have the following values:

Dimensions of the propagation chamber:
    Height=2.5 cm
    Width=2.5 cm
    Length=5 cm
    Dimensions of the separation vessel:
    Width=6 mm
    Residence length=2.5 cm
    Distance from propagation chamber ends=2.5 cm
    Separation surface orientation: centered
    Separation vessel material: acrylic The frequency generator used in this example was manufactured by Exact Electronics, Inc., model no. 528; the power amplifier was manufactured by Electronic Navigation Industries, Inc., model no. 240L RF Power Amplifier; the transducer material was lead zirconate titanate (PZT-4); and, the reflector material was zinc.

The method of the present invention was operated utilizing the following parameters:

Transducer frequency=2 mHz
    Reflector velocity=0.2 mm/sec
    Cycle time for reflector=10 sec
    Input power=50 watts peak
    Output power=5 watts/cm$^2$
    Input feed flow=3 ml/min The original microsphere percentage in the water was about 5% in the continuous flow stream. However, analysis of the products separated according to the procedures of this example showed that there was less than about 0.5% of the microspheres remaining in the water.

EXAMPLE 18

A process within the scope of the present invention is conducted for the purpose of separating microspheres from water. The conditions, structures, parameters, and process are the same as in Example 17, except that the reflector velocity is 0.1 mm/sec.

According to the procedures of this example, excellent separation of the microspheres from the water is visually observable.

EXAMPLE 19

A process within the scope of the present invention is conducted in order to separate microspheres from water. The conditions, structures, parameters, and process are the same as in Example 17, except that the input feed flow is 1 ml/min.

According to the procedures this example, excellent separation of the microspheres from the water is achieved.

E. Double Transducer Embodiment

Figure 9:
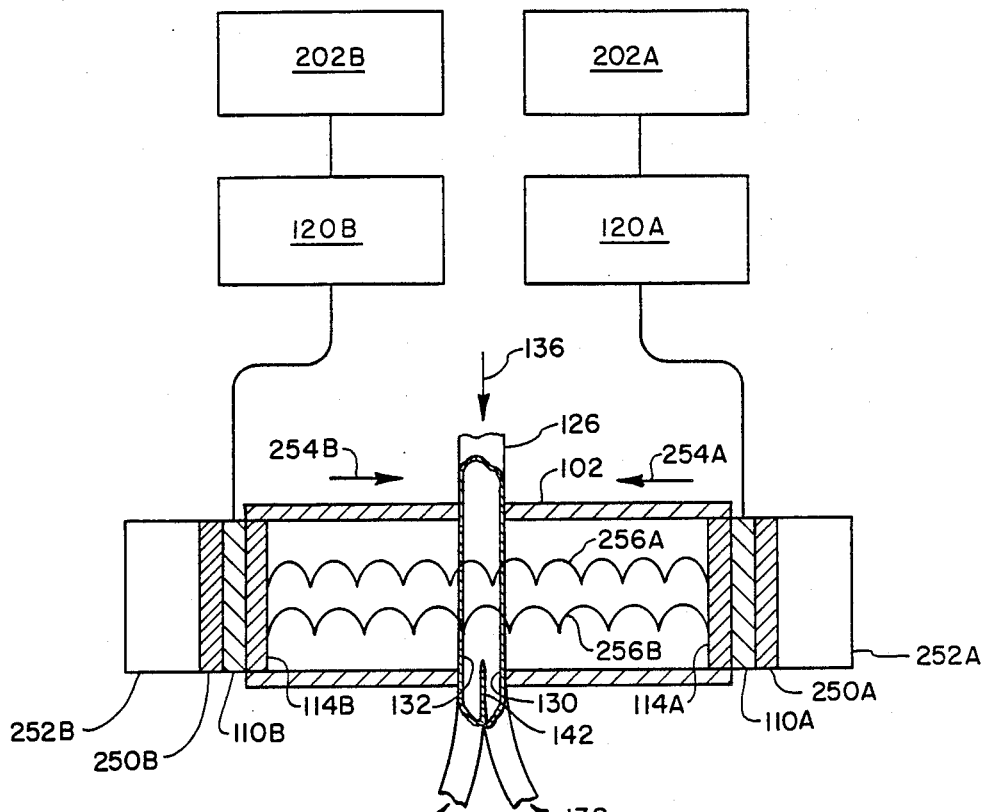

Pseudo-standing waves may also be formed by providing a transducer at each end of propagation chamber 102 and operating each transducer at a slightly different frequency. FIG. 9 shows an elevated cross-section view of the structure of the double transducer embodiment of the present invention.

Similar to the embodiments discussed previously, the double transducer embodiment includes propagation chamber 102 and separation vessel 126 which are constructed considering the same factors as considered in connection with the embodiments shown in FIGS. 7 and 8 above. However, in the double transducer embodiment, transducers 110A and 110B are provided at each end of propagation chamber 102. Each transducer 110A or 110B may be provided with a quarter wave matching section 114A or 114B, respectively, to effect an impedance match between transducer 110A or 110B and the propagation material contained within propagation chamber 102.

Since the embodiment illustrated in FIG. 9 is particularly susceptible to the creation of "true" standing waves some additional structures may be provided to diminish their creation. This is due to the fact that transducers 110A and 110B will reflect some of the acoustic pressure waves incident upon them. Since standing waves are detrimental to the operation of the embodiment a structure may be provided for each transducer, 110A or 110B, which will dampen any acoustic pressure wave impinging upon transducer 110A or 110B. These structures 205A or 205B, which in the present embodiment are composed of absorbent rubber and often termed "absorbers," are coupled to the reverse side of transducers 110A or 110B by second impedance matching sections 252A or 252B, respectively.

Each transducer 110A or 110B is driven by a separate frequency generator 202A or 202B, and power amplifier 120A or 120B, respectively. Both transducers are operated simultaneously—each at a slightly different frequency. The difference in frequencies is chosen as explained later in this section. With both transducers operating, the acoustic pressure wave represented by the wave marked 256A, which is at the same frequency as transducer 110A is operating, propagates in the direction indicated by arrow 254A.

Similarly, the pressure wave marked 256B, which is at the same frequency as transducer 110B is operating, moves in the direction of arrow 254B. Superimposed, these two opposing waves will provide a pseudo-standing wave with moving pressure gradients. The double transducer embodiment has the advantage of allowing transducers 110A and 110B which are operated over a very narrow range of frequencies, and thus exhibit a high "Q", to be used. Such transducers are characteristically more efficient than variable frequency transducers operable over a broad range of frequencies.

With transducer 110A operating at a frequency slightly above the frequency at which transducer 110B is operating, the pressure gradients of the pseudo-standing wave will move in the direction indicated by arrow 254B. The movement of the pseudo-standing wave is expressed mathematically below.

The pressure of the two wave fronts is expressed by Equations G₁ and G₂:

$$P_1 = P_A \sin(\omega_1 t - k_1 z) \tag{G_1}$$

$$P_2 = P_A \sin(\omega_2 t + k_2 z) \tag{G_2}$$

Where:
P = acoustic pressure amplitude of waves 1 and 2
$\omega_1$ = frequency of first transducer
$\omega_2$ = frequency of second transducer
t = time
k = wave number of waves 1 and 2
z = distance from second transducer The superposition of the pressures upon one another gives a new pressure equation. The resultant wave may be expressed by Equation H:

$$P_{(z,t)} = 2 P_A \sin\left[\frac{\omega_1 - \omega_2}{2} t - \frac{k_1 + k_2}{2} z\right] \sin\left[\frac{\omega_1 - \omega_2}{2} t - \frac{k_1 - k_2}{2} z\right] \tag{H}$$

The frequency of the quasi-standing wave can be expressed as set forth in Equation I:

$$\omega_{psw} = \frac{\omega_{inc} + \omega_{ref}}{2} \tag{I}$$

Where:
$\omega_{psw}$ = frequency of the pseudo-standing wave

In addition, the group velocity may be expressed by the same equation as mentioned above and again set for below as Equation J:

$$V_g = \frac{\omega_1 - \omega_2}{k_1 + k_2} = \left(\frac{\omega_1 - \omega_2}{\omega_1 + \omega_2}\right) c \tag{J}$$

Examples of the double transducer embodiment shown in FIG. 9 being used to separate various materials are given below.

EXAMPLE 20

An embodiment within the scope of the present invention and substantially similar to that shown in FIG. 9 above was used in order to separate blood cells from plasma. The dimensions of the structures used in this example have the following values:
Dimensions of the propagation chamber:
Height = 2.5 cm
Width = 2.5 cm
Length = 3.0 cm
Dimensions of the separation vessel:
Width = 6 mm
Residence length = 2.5 cm
Distance from propagation chamber ends = 15 cm
Separation surface orientation: centered
Separation vessel material: urethane rubber The frequency generators used in this example were commercially available radio frequency transceivers; the transducer material was PZT-4; the impedance matching section was fabricated from magnesium.

The method of the present invention was operated utilizing the following parameters:
Transducer frequencies = 2.000001 mHz and 2.0 mHz
Input power = 10 watts peak
Output power = 2 watts/cm²
Input feed flow = 5 ml/min The original blood cell percentage in the plasma was about 26% in the continuous flow stream. However, analysis of the products separated according to the procedures of this example showed that there was less than about 10% of the blood cells remaining in the plasma.

EXAMPLE 21

A process within the scope of the present invention is conducted for the purpose of separating blood cells from plasma. the conditions, structures, parameters, and process are the same as in Example 20, except that the input power is 50 watts peak, the output power is 5 watts/cm², and the input feed flow is 3 ml/min.

According to the procedures of this example, good separation of the blood cells from the plasma is achieved.

EXAMPLE 22

A process within the scope of the present invention is conducted using an embodiment substantially similar to that shown in FIG. 9 for the purpose of separating Phillips crude oil TK-126 dispersed droplets ranging in size from about 1 micron to about 100 microns from water. The dimensions of the structures used for this example have the following values:
Dimensions of the propagation chamber:
Height = 2.5 cm
Width = 2.5 cm
Length = 5 cm Dimensions of the separation vessel:
Width=6 mm
Residence length=2.5 cm
Distance from propagation chamber ends=2.5 cm
Separation surface orientation: centered
Separation vessel material: acrylic The frequency generators for in this example are commercially available radio frequency transceivers; the transducer material is PZT-4; the impedance matching section is fabricated from magnesium.

The method of the present invention is operated utilizing the following parameters:
Transducer frequencies=2.000001 mHz and 2.0 mHz
Input power=50 watts peak
Output power=5 watts/cm$^2$
Input feed flow=3 ml/min According to the procedures for this example, good separation of the oil from the water is achieved.

EXAMPLE 23

A process within the scope of the present invention is conducted for the purpose of separating oil from water. The conditions, structures, parameters, and process are the same as in Example 22, except that the input power is 60 watts peak, the output power is 6 watts/cm$^2$, and the input feed flow is 2 ml/min.

According to the procedures of this example, excellent separation of the oil from the water is achieved.

EXAMPLE 24

An embodiment within the scope of the present invention and substantially similar to that shown in FIG. 9 above was used in order to separate polystyrene microspheres 34 microns in diameter from water. The dimensions of the structures used in this example have the following values:

Dimensions of the propagation chamber:
Height=2.5 cm
Width=2.5 cm
Length=30 cm
Dimensions of the separation vessel:
Width=6 mm
Residence length=7.5 cm
Distance from propagation chamber ends=15 cm
Separation surface orientation: centered
Separation vessel material: urethane The frequency generators used in this example were commercially available radio frequency transceivers; the transducer material was PZT-4; the impedance matching section was fabricated from magnesium.

The method of the present invention was operated utilizing the following parameters:
Transducer frequencies=1.990 mHz and 1.990001 mHz
Input power=10 watts peak
Output power=1 watt/cm$^2$
Input feed flow=1 ml/min The original microsphere percentage in the water was about 1% in the continuous flow stream. However, analysis of the products separated according to the procedures of this example showed that there was less than about 0.1% of the microspheres remaining in the water.

EXAMPLE 25

A process within the scope of the present invention is conducted for the purpose of separating microspheres from water. The conditions, structures, parameters, and process are the same as in Example 24, except that the polystyrene microspheres are 10 microns in diameter and the transducer frequencies are 1.900000 mHz and 1.900001 mHz.

According to the procedures of this example, excellent separation of the microspheres from the water is achieved.

EXAMPLE 26

A process within the scope of the present invention is conducted for the purpose of separating microspheres from water. The conditions, structures, parameters, and process are the same as in Example 24, except that the transducer frequencies are 10 mHz and 10.000003 mHz, the input power is 10 watts peak, and the output power is 1 watt/cm$^2$.

According to the procedures of this example, excellent separation of the microspheres from the water is achieved.

F. Synchronized Moving Reflector/Variable Frequency Embodiment

Analysis of the operation of the variable frequency embodiment shown in FIGS. 6 and 7, and the moving reflector embodiment shown in FIG. 8, will reveal that the power required by transducer 110 to maintain a constant acoustic output power to the propagation material will vary since the frequency will vary. This is due to the fact that the acoustic impedance of the system "seen" by transducer 110 will change as the frequency changes and the frequency of the pressure wave transmitted by transducer 110 sweeps through the resonant nodes of propagation chamber 102.

Figure 10:
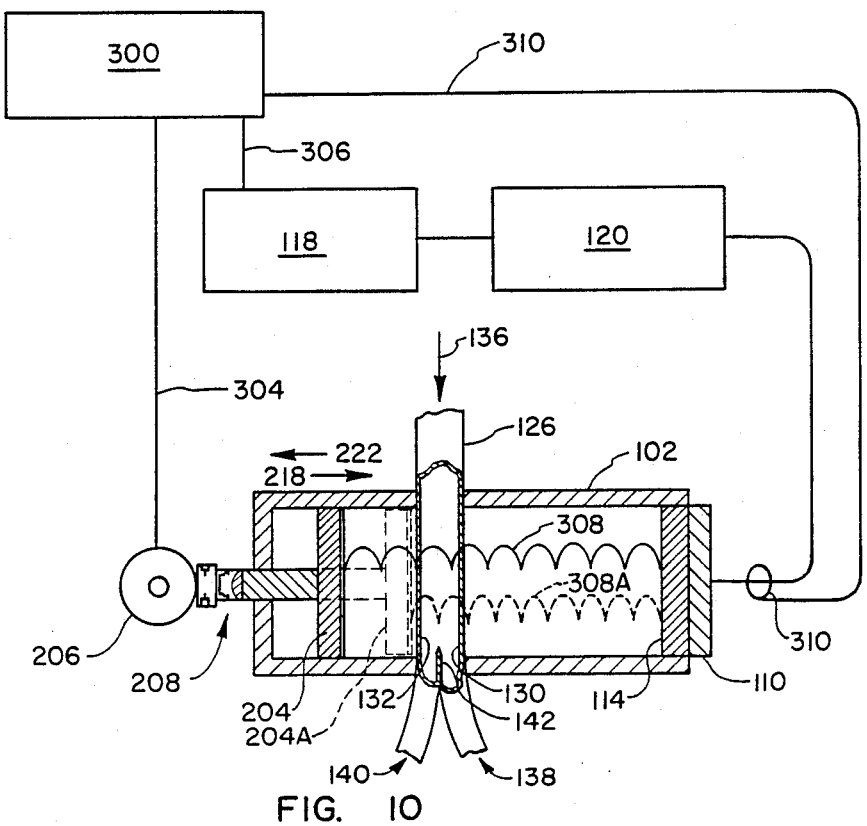

In order to avoid the inefficient use of power input to the transducer that is observed in the variable frequency and moving reflector embodiments the synchronized moving reflector/variable frequency embodiment, shown in FIG. 10, may be used.

As shown in FIG. 10, the synchronized reflector/transducer embodiment is very similar in structure to the moving reflector embodiment, shown in FIG. 8 above. However, fixed frequency generator 202 shown in FIG. 8 has been replaced by a variable frequency generator 118 similar to that used in the variable frequency embodiment shown in FIG. 7. Additionally, a control circuit 300 has been added so as to synchronize the change of frequency by variable frequency generator 118 and the motion of moving reflector 204.

It will be appreciated that it is desirable to maintain the acoustic impedance presented to transducer 110 at a constant value. However, in either the variable frequency or moving reflector embodiments, the acoustic impedance seen by transducer 110 will vary since either the wavelength of the acoustic pressure wave is constantly varying as is the case in the variable frequency embodiment, or the length of the propagation chamber is constantly varying as is the case in the moving reflector embodiment. Combining these two features, and properly synchronizing them, allows the transducer to "see" a constant acoustic impedance which allows the transducer output power to be constantly maintained with a constant input power level.

The operation of the synchronized reflector/frequency embodiment will be explained by reference to FIG. 10. As shown in FIG. 10, a pressure wave 308, generated by transducer 110, travels through propagation chamber towards reflector 204. The wave propagated by transducer 110 ramps upward in frequency as explained above in connection with the variable frequency transducer embodiment. Furthermore, for example, as the frequency transmitted by transducer 110 increases, moving reflector 204 moves toward transducer 110 such that moving reflector 204 is always the same number of wavelengths from transducer 110.

In FIG. 10, this effect has been indicated by showing the position of reflector 204 at a second position, designated 204A. While moving reflector 204 is traveling to the position indicated at 204A, the frequency of the wave being propagated by transducer 110 is increasing. The frequency of the wave propagated by transducer 110 at the time that moving reflector 204 reaches the position indicated at 204A has increased as indicated by the wave form designated 308A. As can be observed in FIG. 10, the number of wavelengths in wave forms 308 and 308A are the same. It should be appreciated that the frequency, and thus the wavelength, of wave forms 308 and 308A are actually constantly changing. However, for clarity, each wave form is shown to possess a constant wavelength.

As will be appreciated by examining FIG. 10, any particles contained within separation vessel 126 will be acted upon by the pressure gradients of acoustic pressure wave 308 so as to be moved toward, and aggregated adjacent to, separation vessel wall 130. When moving piston 204 has reached its point of maximum travel, as indicated at 204A, frequency generator 118 is turned off and moving reflector 204 is returned to its original position. Moving reflector 204 is preferably constructed so as to allow the propagating material to flow 3 through Or around moving reflector 204, while moving reflector is opaque to the acoustic pressure waves propagated through the propagating material. This is easily accomplished by using porous reflecting surfaces known in the art.

The control circuit 300 synchronizes the movement of moving reflector 204 and the frequency of variable frequency generator 118 such that the distance between moving reflector 204 and transducer 110, as expressed in wavelengths of the acoustic pressure wave, is kept constant. Control lines 304 and 306 interconnect control circuit 300 and motor 206 and variable frequency generator 118, respectively. In one embodiment, the power reflected by transducer 110 is monitored as the frequency is altered and the movement of reflector 204 is effected by control circuit 300 in order to maintain minimum reflected power. Line 310 represents the sensing components used to monitor the power input to transducer 110.

By maintaining the distance between moving reflector 204 and transducer 110 a constant number of wavelengths, the acoustic impedance "seen" by transducer 110 is maintained at a constant value. Thus, constant power input to transducer 110 results in a constant output power from transducer 110. In this way, the embodiment shown in FIG. 10 allows a single transducer 110 to be used with a moving reflector 204 to efficiently separate materials possessing different physical properties while still retaining the advantage of allowing the transducer 110 to "see" an acoustic impedance which does not vary.

Examples of the operation and results obtained with use of the synchronized moving reflector/variable frequency transducer embodiment are given below.

EXAMPLE 27

A process within the scope of the present invention is conducted using an embodiment substantially similar to that shown in FIG. 10 above for the purpose of separating blood cells from plasma. The dimensions of the structures for this example have the following values:

Dimensions of the propagation chamber:
Height=2.5 cm
Width=2.5 cm
Length=2.5 cm
Dimensions of the separation vessel:
Width=6 mm
Residence length=2.5 cm
Distance from propagation chamber ends=2.5 cm
Separation surface orientation: centered
Separation vessel material: acrylic The frequency generator for this example is manufactured by Exact Electronics, Inc., model no. 528; the power amplifier is manufactured by Electronic Navigation Industries, Inc., model no. 240L RF Power Amplifier; the transducer material is lead zirconate titanate (PZT-4); the impedance matching section is a half wave transformer and is fabricated from glass; and, the reflector material is zinc.

The method of the present invention is operated utilizing the following parameters:
Transducer frequency=5 MHz
Ramp rate=10 kHz/sec
Ramp direction: upward
Cycle time for ramp=10 sec
Input power=50 watts peak
Output power=20 watts/cm$^2$
Input feed flow=6 ml/min According to the procedures of this example, excellent separation of the blood cells from the plasma is achieved.

EXAMPLE 28

A process within the scope of the present invention is conducted for the purpose of separating blood cells from plasma. The conditions, structures, parameters, and process are the same as in Example 27, except that the ramp rate is 8 kHz/sec and the input feed flow is 4 ml/min.

According to the procedures of this example, excellent separation of the blood cells from the plasma is achieved.

EXAMPLE 29

A process within the scope of the present invention is conducted for the purpose of separating blood cells from plasma. The conditions, structures, parameters, and process are the same as in Example 27, except that the transducer frequency is 2.2 mHz, and the input feed flow is 4 ml/min.

According to the procedures of this example, good separation of the blood cells from the plasma is achieved.

EXAMPLE 30

A process within the scope of the present invention is conducted using an embodiment substantially similar to that shown in FIG. 10 above for the purpose of separating crude oil dispersed into droplets from water. The dimensions of the structures for this example have the following values:

Dimensions of the propagation chamber:

Height=2.5 cm
Width=2.5 cm
Length=5 cm
Dimensions of the separation vessel:
Width=6 mm
Residence length=2.5 cm
Distance from propagation chamber ends=2.5 cm
Separation surface orientation: centered
Separation vessel material: urethane The frequency generator for this example is manufactured Exact Electronics, Inc., model no. 528; the power amplifier is manufactured by Electronic Navigation Industries, Inc., model no. 240L RF Power Amplifier; the transducer material is lead zirconate titanate (PZT-4); the impedance matching section is fabricated from boron nitride; and, the reflector material is aluminum.

The method of the present invention is operated utilizing the following parameters:
Transducer frequency=2.5 MHz
Ramp rate=10 KHz/sec
Ramp direction: upward
Cycle time for ramp=10 sec
Input power=40 watts peak
Output power=5 watts/cm$^2$
Input feed flow=4 ml/min According to the procedure of this example, good separation of the blood cells from the plasma is achieved.

EXAMPLE 31

A process within the scope of the present invention is conducted for the purpose of separating oil from water. The conditions, structures, parameters, and process are the same as in Example 30, except that the transducer frequency is 2 mHz, the ramp direction is downward, the input power is 50 watts peak, the output power is 5 watts/cm$^2$, and the input feed flow was 3 ml/min.

According to the procedures of this example, excellent separation of the oil from the water is achieved.

EXAMPLE 32

A process within the scope of the present invention is conducted using an embodiment substantially similar to that shown in FIG. 10 above for the purpose of separating polystyrene microspheres 34 microns in diameter from water. The dimensions of the structures for this example have the following values:
Dimensions of the propagation chamber:
Height=2.5 cm
Width=2.5 cm
Length=5 cm
Dimensions of the separation vessel:
Width=6 mm
Residence length=2.5 cm
Distance from propagation chamber ends=2.5 cm
Separation surface orientation: centered
Separation vessel material: acrylic The frequency generator for in this example is manufactured by Exact Electronics, Inc., model no. 528 power amplifier is manufactured by Electronic Navigation Industries, Inc., model no. 240L RF Power Amplifier; the transducer material is lead zirconate titanate (PZT-4); and, the reflector material is zinc.

The method of the present invention is operated utilizing the following parameters:
Transducer frequency=7 mHz
Ramp rate=10 kHz/sec
Ramp direction: upward
Cycle time for ramp=10 sec
Input power=40 watts peak
Output power=6 watts/cm$^2$
Input feed flow=3 ml/min According to the procedures of this example, excellent separation of the microspheres from the water is achieved.

EXAMPLE 33

A process within the scope of the present invention is conducted for the purpose of separating microspheres from water. The conditions, structures, parameters, and process are the same as in Example 32, except that the input feed flow is 1 ml/min.

According to the procedures of this example, excellent separation of the microspheres from the water is achieved.

EXAMPLE 34

A process within the scope of the present invention is conducted for the purpose of separating microspheres from water. The conditions, structures, parameters, and process are the same as in Example 32, except that the ramp rate is 5 kHz/sec.

According to the procedures of this example, excellent separation of the microspheres from the water is achieved.

G. Summary

As will be appreciated from the explanation of the invention and description of several embodiments, the present invention provides methods and apparatus for controlling the movement of materials having different physical properties in a fluid. The methods and apparatus of the present invention are significantly more efficient than those methods and apparatus available in the prior art. The present invention allows materials contained within a fluid, whether the materials be particles, immiscible liquids, or undissolved gases, to be controllably moved to a predetermined location. The ability to controllably move materials allows for the efficient separation of those materials from a liquid in which they are suspended.

The present invention, in contrast to the techniques shown in the prior art, may be used to produce either movement or separation of the material without relying on flocculation, sedimentation, centrifugation, the buoyancy of the material, or any other gravity dependent characteristic. The present invention is also able to make use of differing physical separation of the materials. These physical properties include properties such as acoustical properties, the densities of the materials, the volume which the material occupies, and other properties.

Furthermore, the present invention is well-suited for use with either batch processing or continuous flow processing operations. Since the invention is well-suited for continuous flow operations, nearly any desired throughput may be achieved, using the embodiments described herein, by connecting the embodiments in a parallel fashion. Still further, the flexibility of the invention is such that if a high degree of separation is desired, several embodiments may be serially joined so as to allow the continuous flow of the medium to be processed by several of the embodiments.

The present invention also provides that the materials which are being subjected to the process will not be harmed by the process. This attribute, as well as those mentioned above, make the present invention particularly well-suited for processing biological materials, such as separating blood cells from plasma. Still further, the invention is very useful for separating immiscible liquids from one another or undissolved gases from a liquid.

It will be appreciated that the methods and apparatus of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative, and not restrictive, and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for effectuating controlled movement of materials having different physical properties, the method comprising the steps of:
   propagating a first acoustic wave of a first frequency through a separation vessel containing the materials;
   propagating a second acoustic wave of a second frequency through the separation vessel containing the materials, the second acoustic wave having a wavelength which is at least as small as one dimension of the separation vessel, and being different from the first frequency; and
   super imposing the first and second acoustic waves to form a pseudo-standing acoustic wave having a group velocity, said pseudo-standing acoustic wave comprising maximum and minimum pressure surfaces that move with the group velocity of the pseudo-standing acoustic wave, said maximum and minimum pressure surfaces moving at least one of the materials towards a location in the vessel in the direction of the group velocity of the pseudo-standing acoustic wave.

2. A method for effectuating controlled movement of materials having different physical properties as set forth in claim 1, wherein the first acoustic wave is propagated by a first transducer and the second acoustic wave is propagated by a second transducer.

3. A method for effectuating controlled movement of materials having different physical properties as set forth in claim 2, wherein the first and second frequencies are sufficiently high such that cavitation of the materials within the separation vessel is avoided at the power levels used and such that the physical properties and the integrity of the materials are maintained.

4. A method for effectuating controlled movement of materials having different physical properties as set forth in claim 2, wherein the first and second frequencies are within the range of from about one megahertz to about ten megahertz.

5. A method for effectuating controlled movement of materials having different physical properties as set forth in claim 2, wherein the first and second frequencies are within the range of from about two megahertz to about five megahertz.

6. A method for effectuating controlled movement of materials having different physical properties as set forth in claim 2 further comprising the step of attenuating at least some of the reflections of the first and second acoustic waves.

7. A method for effectuating controlled movement of materials having different physical properties as set forth in claim 1, wherein the method further comprises the step of aggregating materials of similar physical properties at the location in the vessel.

8. A method for effectuating controlled movement of materials having different physical properties as set forth in claim 7, wherein at least one of the materials is a biological material.

9. A method for effectuating controlled movement of materials having different physical properties as set forth in claim 8, further comprising the steps of:
   aggregating materials having similar physical properties at the location in the vessel; and
   separating the materials from the remaining materials.

10. A method for effectuating controlled movement of materials having different physical properties as set forth in claim 8, wherein the materials comprise blood cells and plasma and wherein the method further comprises the step of separating the blood cells from the plasma.

11. A method for effectuating controlled movement of materials having different physical properties as set forth in claim 1, further comprising the step of collecting materials having similar physical properties so as to separate such materials from the remaining materials which have different physical properties.

12. A method for effectuating controlled movement of materials having different physical properties as set forth in claim 1, wherein the controlled movement of the materials further comprises the step of moving the materials in a reciprocating motion at periodic intervals so as to agitate the materials.

13. A method for effectuating controlled movement of materials having different physical properties as set forth in claim 1, wherein at least one of the materials comprise particulates and wherein the controlled movement of the materials comprises the step of moving the larger particulates a distance which is different than the distance which the smaller particulates are moved.

14. A method for effectuating controlled movement of materials having different physical properties as set forth in claim 1, wherein the materials comprise particulates and a liquid.

15. A method for effectuating controlled movement of materials having different physical properties as set forth in claim 1, wherein the materials comprise immiscible liquids.

16. A method for effectuating controlled movement of materials having different physical properties as set forth in claim 1, wherein the materials comprise undissolved gas bubbles and a liquid.

17. A method for separating particulates from a particulate suspension, the method comprising the steps of:
   moving the particulates in the particulate suspension in a continuous flow through a separation vessel;
   propagating a first acoustic wave of a first frequency at least as great as one megahertz through the separation vessel;
   propagating a second acoustic wave of a second frequency through the separation vessel, said second frequency being different from the first frequency;
   superimposing the first and second acoustic waves to form a pseudo-standing acoustic wave having a group velocity, said pseudo-standing acoustic wave comprising maximum and minimum pressure surfaces that move with the group velocity of the pseudo-standing acoustic wave, said maximum and minimum pressure surfaces moving at least one of the particles towards a location in the vessel in the direction of the group velocity of the pseudo-standing acoustic wave; and separating at least one of the particulates from the particulate suspension.

18. A method for separating particulates from a particulate suspension as set forth in claim 17, wherein the first acoustic wave is propagated by a first transducer and the second acoustic wave is propagated by a second transducer.

19. A method for separating particulates from a particulate suspension as set forth in claim 18, wherein the first and second frequencies are sufficiently high such that cavitation of the materials within the separation vessel is avoided at the power levels used and such that the physical properties and the integrity of the particles remain intact.

20. A method for effectuating controlled movement of materials having different physical properties as set forth in claim 18 further comprising the step of attenuating at least some of the reflections of the first and second acoustic waves.

21. A method for separating immiscible liquids, the method comprising the steps of:

moving the immiscible liquids in a continuous flow through a separation vessel;

propagating a first acoustic wave of a first frequency at least as great as one megahertz through the separation vessel;

propagating a second acoustic wave of a second frequency through the separation vessel, said second frequency being different form the first frequency;

superimposing the first and second acoustic waves to form a pseudo-standing acoustic wave having a group velocity, said pseudo-standing acoustic wave comprising maximum and minimum pressure surfaces that move with the group velocity of the pseudo-standing acoustic wave, said maximum and minimum pressure surfaces moving at least one of the immiscible liquids towards a location in the vessel in the direction of the group velocity of the pseudo-standing acoustic wave; and separating at least one of the immiscible liquids from the remaining immiscible liquids.

22. A method for separating immiscible liquids as set forth in claim 21, wherein the first acoustic wave is propagated by a first transducer and the second acoustic wave is propagated by a second transducer.

23. A method for separating immiscible liquids as set forth in claim 2, wherein the first and second frequencies are sufficiently high such that cavitation of the immiscible liquids within the separation vessel is avoided at the power level used and such that the physical properties of the immiscible liquids remain intact.

24. A method for effectuating controlled movement of materials having different physical properties as set forth in claim 22 further comprising the step of attenuating at least some of the reflections of the first and second acoustic waves.

25. A method for separating undissolved gases from a liquid, the method comprising the steps of:

moving the undissolved gases and the liquid in a continuous flow through a separation vessel;

propagating a first acoustic wave of a first frequency at least as great as one megahertz through the separation vessel;

propagating a second acoustic wave of a second frequency through the separation vessel, said second frequency being different from the first frequency;

superimposing the first and second acoustic waves to form a pseudo-standing acoustic wave having a group velocity, said pseudo-standing acoustic wave comprising maximum and minimum pressure surfaces that move with the group velocity of the pseudo-standing acoustic wave, said maximum and minimum pressure surfaces moving the undissolved gases towards a location in the vessel in the direction of the group velocity of the pseudo-standing acoustic wave; and separating the undissolved gases from the liquid.

26. A method for separating undissolved gases from a liquid as set forth in claim 25, wherein the first acoustic wave is propagated by a first transducer and the second acoustic wave is propagated by a second transducer.

27. A method for separating undissolved gases from a liquid as set forth in claim 26, wherein the first and second frequencies are sufficiently high such that cavitation of the materials within the separation vessel is avoided at the power level used and such that the physical properties of the undissolved gases remain intact.

28. A method for effectuating controlled movement of materials having different physical properties as set forth in claim 26 further comprising the step of attenuating at least some of the reflections of the first and second acoustic waves.

29. An apparatus for effectuating the controlled movement of materials having different physical properties, the apparatus comprising:

a vessel capable of containing the materials;

means for propagating a first acoustic wave of a first frequency through the vessel; and means for dampening at least some reflections of the first acoustic wave;

means for propagating a second acoustic wave of a second frequency through the vessel, the second frequency being different from the first frequency, the second acoustic wave being propagated such that the first and second acoustic waves interfere with each other to form a pseudo-standing acoustic wave having a group velocity, said pseudo-standing acoustic wave comprising pressure gradients which separate regions of maximum and minimum pressure, said pressure gradients moving through space and time and acting upon at least one of the materials so as to move at least one of the materials towards a location in the vessel in the direction of the group velocity of the pseudo-standing acoustic wave.

30. An apparatus for effectuating the controlled movement of materials having different physical properties as set forth in claim 29, wherein the means for propagating a first acoustic wave comprises a first transducer operating at a first frequency and wherein the means for propagating a second acoustic wave comprises a second transducer operating at a second frequency.

31. An apparatus for effectuating the controlled movement of materials having different physical properties as set forth in claim 30 wherein the means for dampening at least some reflections of the first acoustic wave comprises an acoustic absorber.

32. An apparatus for effectuating the controlled movement of materials having different physical properties as set forth in claim 29 further comprising means for dampening at least some reflections of the second acoustic wave.

33. An apparatus for effectuating the controlled movement of materials having different physical properties as defined in claim 32 wherein the means for dampening at least some reflections of the first acoustic wave comprises an impedance matching section adapted to approximately match the impedance of the second transducer to the medium contained in the vessel.

34. An apparatus for separating materials having different physical properties the apparatus comprising:
   a separation vessel containing the materials;
   means for propagating a first acoustic wave or a first frequency through the separation vessel;
   means for dampening at least some reflections of the first acoustic wave;
   means for propagating a second acoustic wave of a second frequency through the separation vessel, the second frequency being different from the first frequency, the second acoustic wave being propagated such that the first and second acoustic waves interfere with each other to form a pseudo-standing acoustic wave having a group velocity, said pseudo-standing acoustic wave comprising pressure gradients which separate regions of maximum and minimum pressure, said pressure gradients moving through space and time and acting upon at least one of the materials so as to move at least one of the materials to a predetermined location; and
   means for separating the collecting at least one of the materials which has been moved to the predetermined location.

35. An apparatus for separating materials having different physical properties as set forth in claim 34, further comprising means for collecting blood cells and means for collecting plasma.

36. An apparatus for separating materials having different physical properties as set forth in claim 34, further comprising means for collecting particulates and means for collecting a fluid medium.

37. An apparatus for separating the materials having different physical properties as set forth in claim 34, further comprising means for collecting the separated components of immiscible liquids.

38. An apparatus for separating the materials having different physical properties as set forth in claim 34, further comprising means for collecting undissolved gases separated from a liquid.

39. An apparatus for separating materials having different physical properties as set forth in claim 34 further comprising means for dampening at least some reflections of the second acoustic wave.

40. An apparatus for separating materials having different physical properties as set forth in claim 39 wherein the means for dampening at least some reflections of the first acoustic wave comprises an acoustic absorber.

41. An apparatus for separating materials having different physical properties as defined in claim 39 wherein the first transducer comprises a transducer capable of operating at frequencies at least as high as one megahertz.

42. An apparatus for separating materials having different physical properties as set forth in claim 34 wherein the means for propagating a first acoustic wave comprises a first transducer and wherein the means for propagating a second acoustic wave comprises a second transducer.

43. An apparatus for separating materials having different physical properties as defined in claim 42 wherein the means for dampening at least some reflections of the first acoustic wave comprises an impedance matching section adapted to approximately match the impedance of the second transducer to the medium contained in the vessel.

* * * * *

UNITED STATES PATENT AND TRADEMARK OFFICE
CERTIFICATE OF CORRECTION

PATENT NO. : 4,983,189

DATED : January 8, 1991

INVENTOR(S) : STEPHEN C. PETERSON et al.

It is certified that error appears in the above-identified patent and that said Letters Patent is hereby corrected as shown below:

```
Column 3, line 25, "mean" should be --means--
Column 4, line 57, "half way" should be --halfway--
Column 11, line 56, "effects" should be --affects--
Column 11, line 54, "effect" should be --affect--
Column 12, line 26, delete second occurrence of "the"
Column 13, line 12, "mode, that is," should be --mode; that is,--
Column 15, line 62, "some what" should be --somewhat--
Column 17, line 14, delete "s"
Column 17, line 15, "propagation chamber" should be
--propagation chamber 102--
Column 17, line 16, "gradients the" should be --gradients of the--
Column 17, line 28, "cause" should be --causes--
Column 18, line 52, after "velocity" insert --.--
Column 21, line 18, delete "to"
Column 22, line 36, "Width = 6 mn" should be --Width = 6 mm--
Column 24, line 47, "moving reflector" should be --moving reflector
204--
```

UNITED STATES PATENT AND TRADEMARK OFFICE
CERTIFICATE OF CORRECTION

PATENT NO. : 4,983,189

DATED : January 8, 1991

INVENTOR(S) : Stephen C. Peterson et al.

It is certified that error appears in the above-identified patent and that said Letters Patent is hereby corrected as shown below:

```
Column 25, line 31, delete "2."
Column 28, line 36, after "procedures" insert --of--
Column 30, line 49, "the" should be --The--
Column 33, line 33, delete "3"
Column 35, lines 10-11, after "manufactured" insert -- by--
Column 35, line 45, after "microspheres" insert --which are--
Column 35, line 60, delete "is"
```

Signed and Sealed this

Tenth Day of November, 1992

Attest:

DOUGLAS B. COMER

*Attesting Officer*     *Acting Commissioner of Patents and Trademarks*